United States Patent [19]
Still et al.

[11] Patent Number: 5,804,563
[45] Date of Patent: Sep. 8, 1998

[54] SYNTHETIC RECEPTORS, LIBRARIES AND USES THEREOF

[75] Inventors: W. Clark Still, Clinton, N.Y.; Ge Li, Plainsboro, N.J.

[73] Assignee: The Trustees of Columbia University in The City of New York, New York, N.Y.

[21] Appl. No.: 628,972

[22] Filed: Apr. 8, 1996

Related U.S. Application Data

[63] Continuation of Ser. No. 181,628, Jan. 13, 1994, abandoned.

[51] Int. Cl.⁶ ..................................................... A01N 45/00
[52] U.S. Cl. ........................... 514/26; 530/333; 530/334; 530/300; 536/1.11; 536/4.1; 536/23.1; 536/25.3; 536/25.32; 536/5; 514/44; 514/48; 552/101; 552/200; 552/208; 564/1
[58] Field of Search ....................... 435/6, 7.1; 436/501, 436/518, 528, 529, 531, 534; 530/333, 334, 300; 536/1.11, 4.1, 23.1, 25.3, 25.32, 5; 514/26, 44, 48; 552/101, 200, 208; 564/1

[56] References Cited

U.S. PATENT DOCUMENTS

| | | |
|---|---|---|
| 4,354,972 | 10/1982 | Kaiser . |
| 4,833,092 | 5/1989 | Geysen . |
| 5,010,175 | 4/1991 | Rutter et al. . |
| 5,133,866 | 7/1992 | Kauvar . |
| 5,182,366 | 1/1993 | Huebner et al. . |
| 5,194,392 | 3/1993 | Geysen . |
| 5,225,533 | 7/1993 | Rutter et al. . |
| 5,252,296 | 10/1993 | Zuckermann et al. . |
| 5,266,684 | 11/1993 | Rutter et al. . |
| 5,270,170 | 12/1993 | Schatz et al. . |
| 5,288,514 | 2/1994 | Ellman . |

FOREIGN PATENT DOCUMENTS

| | | |
|---|---|---|
| WO9117823 | 11/1991 | WIPO . |
| WO9200091 | 1/1992 | WIPO . |
| WO9209300 | 6/1992 | WIPO . |
| WO9210588 | 6/1992 | WIPO . |
| WO9306121 | 4/1993 | WIPO . |
| WO9312427 | 6/1993 | WIPO . |
| WO9319205 | 9/1993 | WIPO . |
| WO9320242 | 10/1993 | WIPO . |
| WO9402515 | 2/1994 | WIPO . |
| WO9404558 | 3/1994 | WIPO . |
| WO9406017 | 3/1994 | WIPO . |
| WO9406291 | 3/1994 | WIPO . |

OTHER PUBLICATIONS

Bunin et al "A General and Expedient Method for the Solid Phase Synthesis of 1,4–Benzodiazapine Derivatives" JACS 114 pp. 10997–10998, 1992.

Bonar–Law et al., Agnew. Chem. Int. Ed. Eng., vol. 29, No. 12, (1990) "Artificial Receptors for Carbohydrate Derivatives".

Hirschmann et al., J. Am. Chem. Soc.,,vol. 114, pp. 9699–9701 (1992) "The First Design and Synthesis of a Steroidal Peptidomimetic. The Potential Value of Peptidomimetics in Elucidating the Bioactive Conformation of Peptide Ligands".

Yoon et al., J. Am. Chem. Soc., vol. 115, pp. 823–824 (1993) "An Exceptional Synthetic Receptor for Peptides".

Tor et al., J. Am. Chem. Soc., vol. 114, pp. 6653–6661 (1992) "Tripodal peptides with Chiral Conformations Stabalized by Intrastrand Hydrogen Bonds".

Kartha et al., Acta Cryt. vol. B31, pp. 2035–2039 (1975) "The Crystal Structure and Molecular Conformation of Cyclo–L–Prolyl–L–prolyl–L–hydroxyproline, a cyclic tripeptide".

Rubek, Jr. 1991, *Host–guest molecular interactions: from chemistry to biology.* Wiley, Chichester, pp. 98–114 "Clefts as receptor and enzyme analogs".

Akerfeldt, A. et al., "Tetraphilin: A Four–Helix Proton Channel Built on a Tetraphenylporphyrin Framework," Journal of the American Chemical Society (1992), vol. 114, pp. 9656–9657.

Alper, J., "Oligonucleotides Surge into Clinical Trials," Bio/Technology (1993), vol. 11, p. 1225.

Amato, I., "Speeding Up a Chemical Game of Chance," Science (1992), vol. 257, pp. 330–331.

Armstrong, D.W. and DeMond, W., "Cyclodextrin Bonded Phases For the Liquid Chromatographic Separation of Optical, Geometrical, and Structural Isomers," Journal of Chromatographic Science (1984), vol. 22, pp. 411–415.

Atassi, M.Z. and Zablocki, W., "Can an Antibody–combining Site Be Mimicked Synthetically? The Possible Surface Simulation Synthesis of Two Antibody–Combining Sites Complementary to Two Antigenic Sites of Lysozyme," Journal of Biological Chemistry (1977), vol. 252, pp. 8784–8787.

Baum, R., "Solid–phase Synthesis of Benzodiazepines," C & E News (1993), vol. 71, pp. 33–34.

Baum, R., "Combinatorial Approaches Provide Fresh Leads for Medicinal Chemistry," C & E News (1994), vol. 72, pp. 20–26.

Bhattarai, K.M., et al., "Diastereo–and Enantio–selective Binding of Octyl Glucosides by an Artificial Receptor," Journal of the Chemical Society: Chemical Communications (1992), pp. 752–754.

(List continued on next page.)

*Primary Examiner*—Paula K. Hutzell
*Assistant Examiner*—Heather A. Bakalyar
*Attorney, Agent, or Firm*—Heslin & Rothenberg, PC

[57] ABSTRACT

The invention is directed to synthetic receptor(s) which comprises a polyfunctional organic template covalently linked to two or more oligomers which may independently be the same or different and may independently be straight chain or branched. The template may be linked to an identifier which uniquely defines the synthetic receptor. The identifier is a stable chemical molecule or a plurality of stable chemical molecules distinguishable and detectable to picomolar levels or may be an oligonucleotide. In an preferred embodiment, the template is covalently linked to a solid support which is linked to an identifier.

14 Claims, 6 Drawing Sheets

OTHER PUBLICATIONS

Blake, J. and Litzi–Davis, L., "Evaluation of Peptide Libraries: An Iterative Strategy to Analyze the Reactivity of Peptide Mixtures with Antibodies," Bioconjugate Chem. (1992), vol. 3, pp. 510–513.

Bock, L.C. et al., "Selection of Single–stranded DNA Molecules that Bind and Inhibit Human Thrombin," Nature (1992), vol. 355, pp. 564–566.

Bonar–Law, R.P. and Sanders, J.K.M., "Cyclocholates: Synthesis and Ion Binding," Tetrahedron Letters (1993), vol. 33, pp. 2071–2074.

Bonar–Law, R.P. and Sanders, J.K.M., "Self–Associating Cyclocholates," Tetrahedron Letters (1993), vol. 34, pp. 1677–1680.

Borchardt, A. and Still, W. C., "Synthetic Receptor Binding Elucidated with an Encoded Combinatorial Library," J. Am. Chem. Soc. (1994), vol. 116, pp. 371–372.

Borman, S., "DNA Oligomers Inhibit Enzyme Activity," C & E News (1992), vol. 70, p. 5.

Bray, A.M. et al., "The Simultaneous Multiple Production of Solution Phase Peptides; Assessment of the Geysen Method of Simultaneous Peptide Synthesis," Tetrahedron Letters (1990), vol. 31, pp. 5811–5814.

Brenner, S. and Lerner, R.A., "Encoded Combinatorial Chemistry," Proc. Natl. Acad. Sci. USA (1992), vol. 89, pp. 5381–5383.

Brummel, C.L. et al., "A Mass Spectrometric Solution to the Address Problem of Combinatorial Libraries," Science (1994), vol. 264, pp. 399–402.

Carpino, L.A. and Chao, H.G., "((9–Fluorenylmethyl)oxy) carbonyl Amino Acid Chlorides in Solid–Phase Peptide Synthesis," Journal of Organic Chemistry (1991), vol. 56, pp. 2635–2642.

Cho, C.Y. et al., "An Unnatural Biopolymer," Science (1993), vol. 261, pp. 1303–1305.

Chu, Y. and Whitesides, G.M., "Affinity Capillary Electrophoresis Can Simultaneously Measure Binding Constants of Multiple Peptides to Vancomycin," Journal of Organic Chemistry (1992), vol. 57, pp. 3524–3525.

Danheiser, S.L., "Current Trends in Synthetic Peptide and Chemical Diversity Library Design," GEN (1994), vol. 14, pp. 10 and 31.

Dimond, P.F., "Pharmacopeia Inc.'s Novel Molecular Tagging System Finds Molecules," GEN (1994), vol. 14, pp. 32 and 38.

Fisher, L.M., "New Drugs by Process of Elimination," New York Times (1992), vol. 142, pp. D1 and D13.

Fodor, S.P.A. et al., "Light–Directed, Spatially Addressable Parallel Chemical Synthesis," Science (1991), vol. 251, pp. 767–773.

Furka, A. et al., "More Peptides by Less Labour," Abstract 10th Intl. Symp. Med. Chem., Budapest, Hungary (1988), p. 288.

Furka, A., et al., "General method for rapid synthesis of multicomponent peptide mixtures," International Journal of Peptide & Protein Research (1991), vol. 37, pp. 487–493.

Furka, A. et al., "Cornucopia of Peptides by Synthesis," Abstract 14th Int. Congr. Biochem., Prague, Czechoslovakia (1988), vol. 5, p. 47.

Geysen, H.M. et al., "Use of Peptide Synthesis to Probe Viral Antigens for Epitopes to a Resolution of a Single Amino Acid," Proc. Natl. Acad. Sci. USA (1984), vol. 81, pp. 3998–4002.

Geysen, H.M. and Mason, T.J., "Screening Chemically Synthesized Peptide Libraries for Biologically–Relevant Molecules," Bioorganic and Medicinal Chemistry Letters (1993), vol. 3, pp. 397–404.

Ghadiri, M.R., et al. "Design of an Artificial Four–Helix Bundle Metalloprotein via a Novel Ruthenium (II)–Assisted Self–Assembly Process," Journal of the American Chemical Society (1992), vol. 114, pp. 4000–4002.

Grimsrud, E.P., "The Electron Capture Detector," Detectors for Capillary Chromatography, Hill, H.H. and McMinn, D.G. editors, John Wiley and Sons, Inc. (1992), pp. 83–107.

Harlow, E. and Lane, D., editors, "Antibody Capture Assays–Detecting and Quantitating Antigens Using Antibody Excess Assays," Antibodies: A Laboratory Manual, Cold Spring Harbor Laboratory (1988), pp. 570–573.

Hong, J., et al., "Highly Selective Binding of Simple Peptides by a $C_3$ Macrotricyclic Receptor," Journal of the American Chemical Society (1991), vol. 113, pp. 5111–5112.

Houghten, R.A., "General Method for the Rapid Solid–Phase Synthesis of Large Numbers of Peptides: Specificity of Antigen–Antibody Interaction at the Level of Individual Amino Acids," Proc. Natl. Acad. Sci. USA (1985), vol. 82, pp. 5131–5135.

Houghten, R.A., "Simultaneous Multiple Peptide Synthesis: The Rapid Preparation of Large Numbers of Discrete Peptides for Biological, Immunological, and Methodological Studies," BioTechniques (1986), vol. 4, pp. 522–528.

Houghten, R.A. et al., "Generation and Use of Synthetic Peptide Combinatorial Libraries for Basic Research and Drug Discovery," Nature (1991), vol. 354, pp. 84–86.

Houghton, A.N. and Scheinberg, D.A., "Monoclonal Antibodies: Potential Applications to the Treatment of Cancer," Seminars in Oncology (1986), vol. 13, pp. 165–179.

Jung, G. and Beck–Sickinger, A.G., "Multiple Peptide Synthesis Methods and Their Applications," Angew. Chem. Int. Ed. Engl. (1992), vol. 31, pp. 367–383.

Karle, I.L. et al., "Modular Design of Synthetic Protein Mimics, Crystal Structure of Two Seven–Residue Helical Peptide Segments Linked by $\epsilon$–Aminocaproic Acid," Journal of the American Chemical Society (1991), vol. 113, pp. 3952–3956.

Kerr, J.M. et al., "Encoded Combinatorial Peptide Libraries Containing Non–Natural Amino Acids," J. Am. Chem. Soc. (1993), vol. 115, pp. 2529–2531.

Lam, K.S. et al., "A New Type of Synthetic Peptide Library for Identifying Ligand–Binding Activity," Nature (1991), vol. 354, pp. 82–84.

Lam, K.S., et al., "The Chemical Synthesis of Large Random Peptide Libraries and Their Use for the Discovery of Ligands for Macromolecular Acceptors," Bioorganic & Medicinal Chemistry Letters (1993), vol. 3, No. 3, pp. 419–424.

Liu, R. and Still, W.C., "Highly Selective Binding of Diverse Neutral Donor/Acceptor Substrates by a $C_3$ Macrotricyclic Receptor," Tetrahedron Letters (1993), vol. 34, No. 16, pp. 2573–2576.

McCormick, D.J. and Atassi, M.Z., "Localization and synthesis of the acetylcholine–binding site in the $\alpha$–chain of the *Torpedo californica* acetylcholine receptor," Biochemical Journal (1984), vol. 224, pp. 995–1000.

Merrifield, B., "Solid Phase Synthesis," Science (1986), vol. 232, pp. 341–347.

Morii, T., et al., "Sequence–Specific DNA Binding by a Geometrically Constrained Peptide Dimer," Journal of the American Chemical Society (1993), vol. 115, pp. 1150–1151.

Mutter, M. and Vuilleumier, S., "A Chemical Approach to Protein Design: Template–Assisted Synthetic Proteins (TASP),"Angewandte Chemie (1989), vol. 28, pp. 535–676.

Mutter, M. et al., "Template–Assembled Synthetic Proteins with Four–Helix–Bundle Topology. Total Chemical Synthesis and Conformational Studies," Journal of the American Chemical Society (1992), vol. 114, pp. 1463–1470.

Needels, M.C. et al., "Generation and Screening of an Oligonucleotide–Encoded Synthetic Peptide Library," Proc. Natl. Acad. Sci. USA (1993), vol. 90, pp. 10700–10704.

Nelson, B., "Bar Code System Helps Scientists Identify New Compounds For Drugs," Columbia University Record (1994), vol. 19, p. 3.

Nielsen, J. et al., "Synthetic Methods for the Implementation of Encoded Combinatorial Chemistry," J. Am. Chem. Soc. (1993), vol. 115, pp. 9812–9813.

Ohlmeyer, M.H.J. et al., "Complex Synthetic Chemical Libraries Indexed with Molecular Tags," Proc. Acad. Sci. USA (1993), vol. 90, pp. 1464–1468.

Pavia, M.R. et al., "The Generation of Molecular Diversity," Bioorganic & Medicinal Chemistry Letters (1993), vol. 3, pp. 387–396.

Roux, K.H., et al., "Construction of an extended three–dimensional idiotope map by electron microscopic analysis of idiotope analysis of idiotope–anti idiotope complexes," Proceedings of the National Academy of Sciences (1987), vol. 84, pp. 4665–5086.

Schultz, P.G., "Catalytic Antibodies," Accounts of Chemical Research (1989), vol. 22, pp. 287–294.

Schwabacher, A.W. and Lei, H., "A New Assay for Molecular Recognition," Journal of Organic Chemistry (1990), vol. 55, pp. 6080–6081.

Smith, P.W., et al., "Molecular Complex Evaluation: A Simultaneous Assay of Binding Using Substrate Mixtures," Journal of Organic Chemistry (1988), vol. 53, No. 7, pp. 1587–1590.

Stone, D., "The Hot New Field of Molecular Diversity," Bio/Technology (1993), vol. 11, pp. 1508–1509.

Waldmann, T.A., "Monoclonal Antibodies in Diagnosis and Therapy," Science (1991), vol. 252, pp. 1657–1662.

Yee, C., et al., "Biocatalytic Resolution of Tertiary α–Substituted Carboxylic Acid Esters: Efficient Preparation of a Quaternary Asymmetric Carbon Center," Journal of Organic Chemistry (1992), vol. 57, pp. 3525–3527.

A TYPICAL DECODING GAS CHROMATOGRAPHY SPECTRUM OF A SINGLE BEAD.

SYNTHETIC RECEPTORS, LIBRARIES AND USES THEREOF

This is a continuation of application Ser. No. 08/181,628, filed Jan. 13, 1994, now abandoned.

The invention was made in part with government funds under Grant CHE92-08254 from the National Science Foundation. Therefore, the U.S. Government has certain rights in the invention.

Throughout this application, various references are referred to within parentheses. Disclosure of these publications in their entireties are hereby incorporated by reference into this application to more fully describe the state of the art to which this invention pertains.

BACKGROUND OF THE INVENTION

Receptors are molecules which selectively interact with other molecules. Receptor molecules perform a variety of tasks from selective binding of substrates to catalyzing chemical reactions. One example of a multifunctional receptor molecule is monoclonal antibodies. Monoclonal antibodies bind to other molecules (antigens) with very high selectivity, while in other cases they catalyze chemical reactions by selectively binding the transition states of those chemical reactions. Monoclonal antibodies are used as medicinal and diagnostic agents. Other receptor molecules are used as drug targeting molecules and are sometimes referred to as "magic bullets". In all cases, the receptor molecules effectiveness is dependent upon its ability to bind molecular species (substrates) with high discrimination and selectivity, i.e. not bind other often closely related molecular species.

Antibodies are proteins produced in response to the presence of a foreign substrate (Stryer, L. Biochemistry, 3rd Edition, W. H. Freeman and Company, New York, 1988 and Schultz, P. G. Acc. Chem. Res., 1989, 22, 287). A foreign substrate capable of eliciting antibody formation is called an antigen. Each antibody has a highly specific affinity for the antigen which stimulated its synthesis.

The free energy for an antibody binding its antigen is normally from 6–15 kcal/mol. Structure analysis of antibodies have indicated that most have an immunoglobulin structure. Immunoglobulins are flexible Y-Shape molecules and consists of two kinds of polypeptide chains named as light and heavy chains molecular weight (FIG. 1).

While other workers have used combinatorial methods to prepare peptide and oligomer libraries, applications are the first to apply combinatorial techniques to generate receptor libraries and to methods to identify receptors for specific biological targets.

SUMMARY OF THE INVENTION

The invention is directed to synthetic receptor(s) which comprises a polyfunctional organic template covalently linked to two or more oligomers which may independently be the same or different and may independently be straight chain or branched. The template may be linked to an identifier which uniquely defines the synthetic receptor. The identifier is a stable chemical molecule or a plurality of stable chemical molecules distinguishable and detectable to picomolar levels or may be an oligonucleotide. In an preferred embodiment, the template is covalently linked to a solid support which is linked to an identifier.

In addition, the invention includes methods of preparing synthetic receptors and synthetic receptor libraries. The synthetic library may be linked with identifiers such that the library comprises a plurality of different synthetic receptor members. The invention also provides methods for assaying a synthetic receptor library to determine suitable synthetic receptor(s) which (a) bind an acceptor molecule; (b) exhibit biological activity; and (c) which catalyze a reaction or inhibit a catalyzed reaction.

BRIEF DESCRIPTION OF THE DRAWINGS

FIG. 1 illustrates an IgG molecule. Both L (light) and H (heavy) chains consist of a variable (V) and constant (C) region. The variable regions of light chain ($V_L$) and heavy chain ($V_H$) are similar in the length and sequence. Immunoglobulin G can be cleaved into three fragments. Two of these fragments bind antigen. They are named as $F_{ab}$ (ab stands for antigen-binding, F for fragments). Each $F_{ab}$ contains one combining site (or antigen-binding site) for antigen, and it has the same binding affinity for antigen as does the whole molecule. The other fragment, called Fc because it crystallizes readily, does not bind an antigen. As indicated in FIG. 1, $F_{ab}$ contains four subunits $V_L$, $V_H$, $C_L$ and $C_{H1}$.

FIG. 2 illustrates the combinatorial method of split-synthesis used to generate 27 tripeptides on a solid support.

FIG. 3 illustrates the process used to monitor reactions on solid supports.

FIG. 4 illustrates the color screening assay using Disperse Red to detect the members of receptor library on beads that bind a substrate.

FIG. 5 illustrates the reading of the molecular bar code from a single synthesis bead.

FIG. 6 illustrates a typical gas chromatography spectrum for a single decoded bead. (The binary encoding system with molecular tags was used).

DETAILED DESCRIPTION OF THE INVENTION

Figure 1:
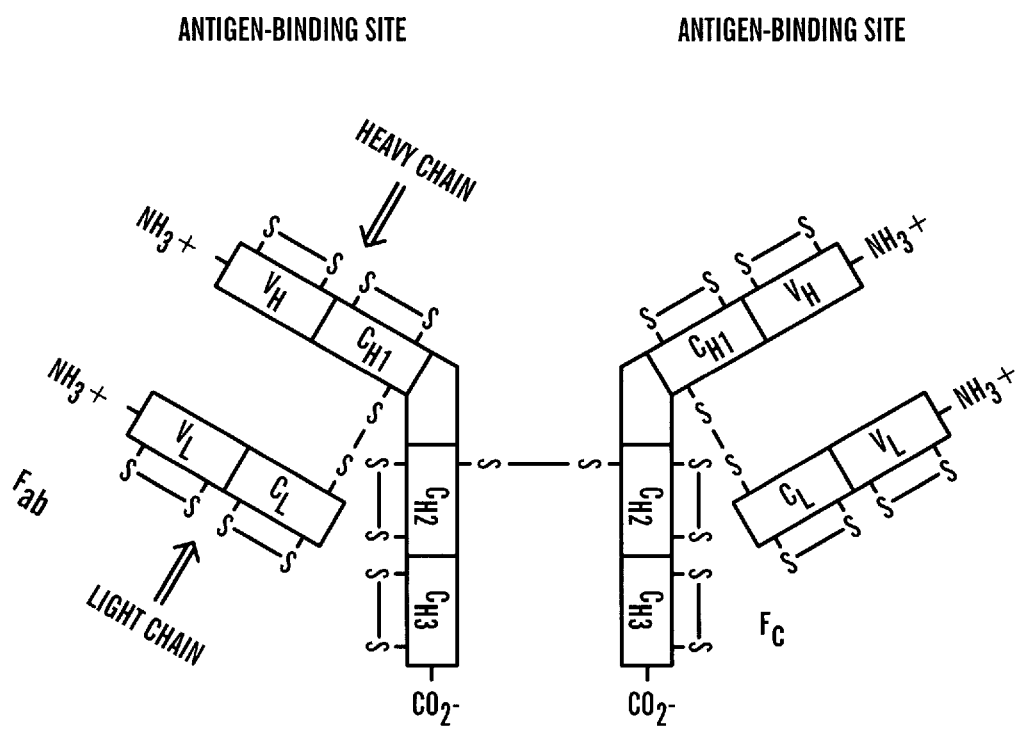
FIG. 1.

As used herein, a polyfunctional organic template is (a) a monocyclic aliphatic hydrocarbon, (b) a polycyclic aliphatic hydrocarbon, (c) a monocyclic aromatic hydrocarbon, (d) a polycyclic aromatic hydrocarbon, (e) a monocyclic heterocycle, (f) a polycyclic heterocycle, or (g) a macrocycle.

As used herein, an oligomer includes homomers and heteromers and oligomers include an oligoamide, an oligoester, an oligourea, an oligourethane, an oligoamine, an oligoether, an oligosulfonamide, an oligophosphonamide, an oligophosphonate, an oligophosphate, an oligonucleotide, an oligosaccharide, a peptide oligomer or a mixture of monomers thereof As used herein, covalently linked is a linkage such as an ester bond, an amide bond, an amine bond, an ether bond, or a linkage through a sulfur, silicon, nitrogen, oxygen, carbon atom, or a covalent bond to any suitable atom.

This invention is directed to a synthetic receptor comprising a polyfunctional organic template covalently linked to two or more oligomers which may independently be the same or different and may independently be straight chain or branched. The polyfunctional organic template may be a polycarbocyclic, a polycyclic hydrocarbon, a polyheterocyclic, a macrocyclic polyether, a macrocyclic polyamine, a macrocyclic polyamide, macrocyclic polyester, a macrobicycle, a macrotricycle, a macrotetracycle, a podand or

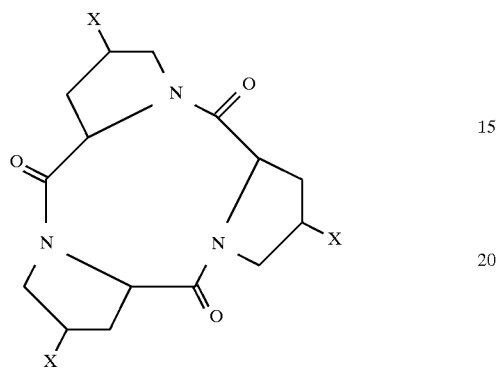

where X=OH, SH or $NH_2$,

Other polyfunctional organic templates include porphyrin rings, cyclodextrins, oligoprolines, calixeranes and macrocycles of the type shown below

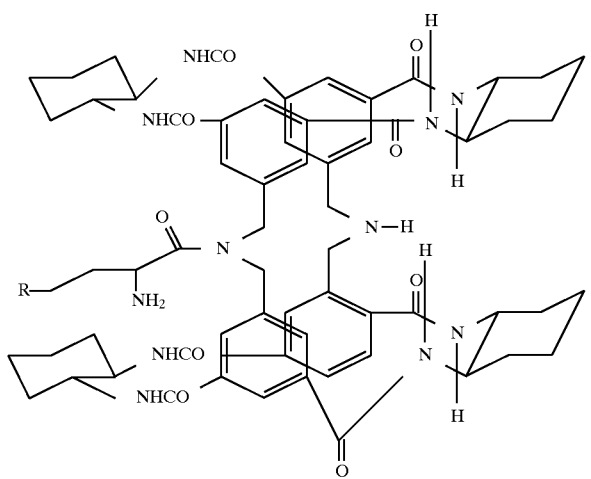

or

-continued

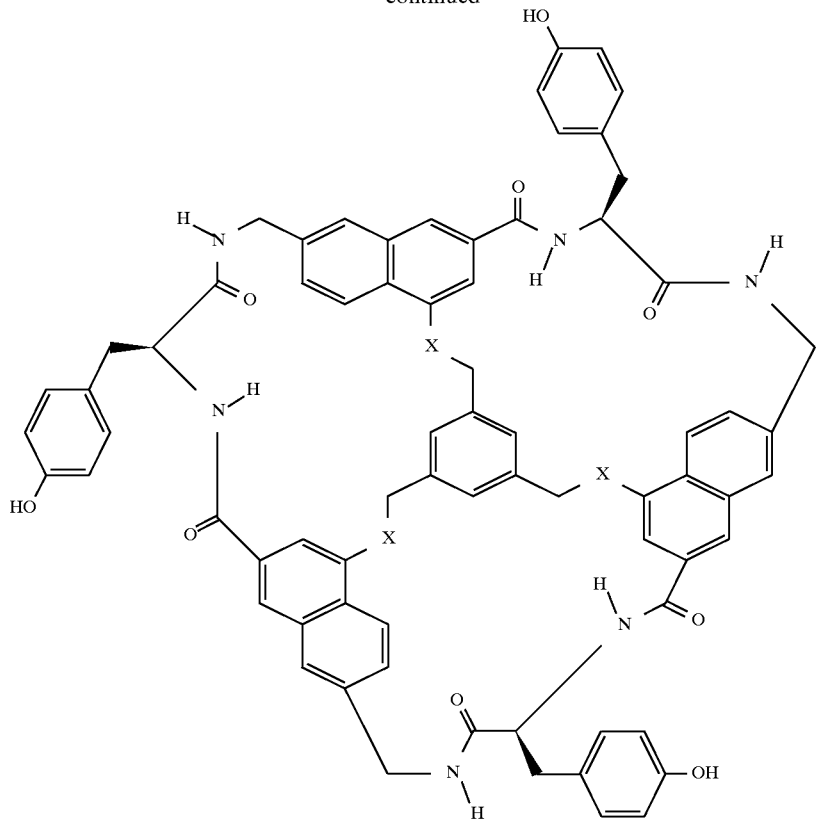

where X=O or S,

In addition the following are also suitable polyfunctional organic templates,

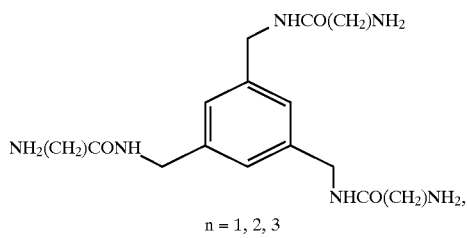

n = 1, 2, 3 or

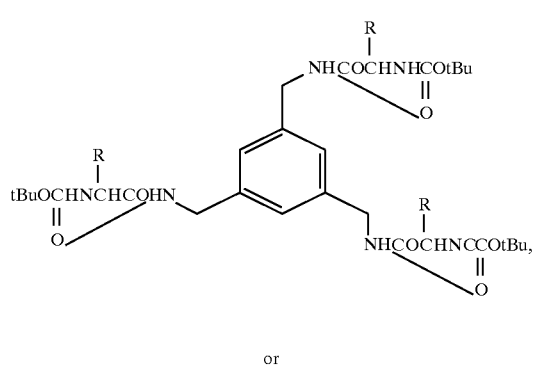

or

-continued

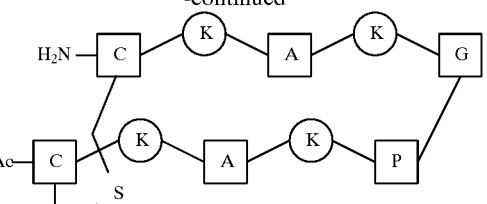

where K=lysine or

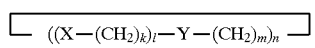

where X,Y=O, S, NH; k,m=2–6; l=0–5; and n=1–6.

The cyclic heterocycle may be a cyclic polypeptide such as cyclosporin

where n=3–20.

The oligomer may be an oligoamide, an oligoester, an oligourea, an oligourethane, an oligoamine, an oligoether, an oligosulfonamide, an oligophosphonamide, an oligophosphonate, an oligophosphate, an oligonucleotide, an oligosaccharide, a peptide oligomer or a mixture of monomers thereof. In one preferred embodiment of the invention each oligomer contains less than ten monomers. The oligomers of the synthetic receptor may be the same or different. In another preferred embodiment at least one of the oligomers is a combination of two or more distinct classes of oligomers selected from the group consisting of the above mentioned oligomers. The oligomer may be a heteromer or a homomer.

In one embodiment of the invention the synthetic receptor may be a polyfunctional steroid template covalently linked to two or more peptide oligomers which may independently be the same or different and which may independently be straight chain or branched.

The polyfunctional steroid template may be ursodeoxycholic acid, hyodeoxycholic acid, alpha-apocholic acid,

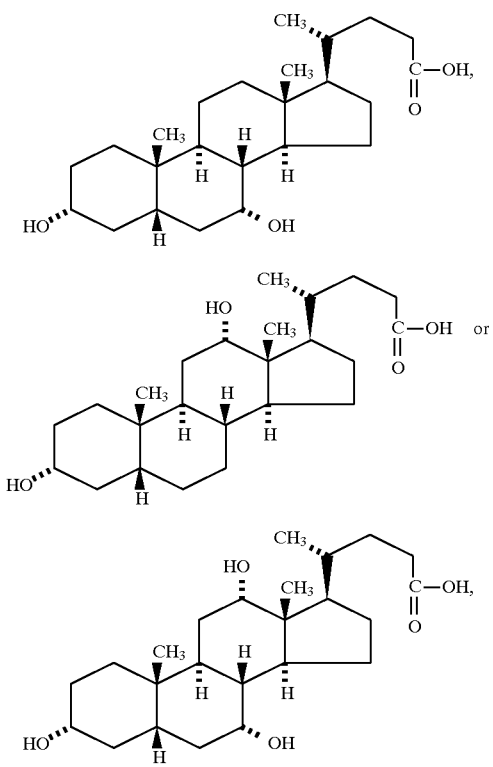

In the preferred embodiment where the synthetic receptor comprises a polyfunctional steroid template the oligomer may be a peptide oligomer comprising at least two amino acids. The template may be further linked to a dye, a fluorescent label or a radioactive label. In addition, the polyfunctional organic template may further be linked to an identifier which uniquely defines the synthetic receptor. The identifier uniquely defines the synthesis and molecular structure of the oligomers of the synthetic receptor. The identifier is a stable chemical molecule or a plurality of stable chemical molecules distinguishable and detectable to picomolar levels or may be an oligonucleotide.

In a preferred embodiment, the synthetic receptor may be a polyfunctional organic template covalently linked to a solid support and to two or more oligomers which may independently be the same or different and which may independently be straight chain or branched. The solid support is preferably a particle composed of cellulose, controlled-pore glass, silica gel, polystyrene, PEG-polystyrene, polystyrene optionally cross-linked with divinylbenzene, grafted co-poly, poly-acrylamide, latex, polydimethylacrylamide optionally cross-linked with N,N'-bis-acryloyl ethylene diamine, glass coated with a polymer, or low molecular weight non-cross-linked polystyrene and the particle is a spheroid, a capillary, a hollow fiber, a needle, or a solid fiber.

In the case where the polyfunctional organic template is a steroid, the template it is covalently linked to polystyrene or PEG-polystyrene particles. The solid support is further linked to an identifier which uniquely identifies the synthetic receptor covalently linked to the solid support.

The invention provides methods to prepare libraries comprising a plurality of distinct synthetic receptors, where the libraries comprise at least 100 distinct synthetic receptors. The libraries comprise at least $10^3$ distinct synthetic receptors and in some instances $10^6$ and in other instances $10^9$ distinct synthetic receptor members. The libraries may have synthetic receptors where the polyfunctional organic template is an acyclic hydrocarbon, a monocyclic aliphatic hydrocarbon, a polycyclic aliphatic hydrocarbon, a monocyclic aromatic hydrocarbon, a polycyclic aromatic hydrocarbon, a monocyclic heterocycle, a polycyclic heterocycle, a macrocycle or a steroid. In one embodiment the synthetic receptors of the libraries are covalently linked to a solid support. The libraries may have at least 100 unique solid supports. The solid support is linked to an identifier or identifiers which uniquely define the synthetic receptors. In other preferred embodiments, the polyfunctional organic template is further linked to an identifier or identifiers.

In addition, the invention provides a method of preparing a synthetic receptor library with identifiers comprising a plurality of different synthetic receptor members. Each synthetic receptor library member may be a solid support having a single type of synthetic receptor attached. The method having the following steps:

a) reacting the solid supports in a reaction vessel with a polyfunctional organic template;

b) apportioning the solid supports with the attached polyfunctional organic template among a plurality of reaction vessels;

c) reacting the polyfunctional organic template on a solid support in each reaction vessel with a first oligomer monomer;

d) reacting the solid supports in each reaction vessel with a first identifier;

e) pooling the solid supports;

f) apportioning the pooled supports among a plurality of reaction vessels;

g) reacting the polyfunctional organic template on solid support in each reaction vessel with a second oligomer monomer;

h) reacting the pooled solid supports in each reaction vessel with a second identifier; and i) repeating steps (e) through (h) from at least one to twenty times for each oligomer of the synthetic receptor.

The invention also provides a method comprising the steps of:

a) preparing a bifunctional solid support containing a first type of active site blocked with a first type of protecting group and a second type of active site blocked with a second type of protecting group;

b) reacting the solid support with an activator to remove the first type of protecting group thereby exposing the first type of active site;

c) coupling a protected polyfunctional organic template to the first type of active site;

d) reacting the protected polyfunctional organic template with an activator to remove the first type of protecting group thereby exposing the first type of active site;

e) coupling a protected oligomer monomer to the deprotected polyfunctional organic template;

f) reacting the solid support with an activator to remove the second type of protecting group thereby exposing the second type of active site;

g) coupling a protected identifier to the second type of active site; and h) repeating steps (d) through (g) from one to twenty times for each oligomer of the synthetic receptor.

The invention also provides the method comprising the steps of:

a) coupling a protected polyfunctional organic template to a solid support;

b) reacting the protected polyfunctional organic template with an activator to remove the protecting group thereby exposing the active site;

c) coupling a protected oligomer monomer to the deprotected polyfunctional organic template;

d) coupling an identifier to the solid support; and e) repeating steps (b) through (d) from one to twenty times for each oligomer of the synthetic receptor.

Another embodiment of the invention is a method of preparing a synthetic receptor with one or more identifiers which comprises a polyfunctional organic template covalently linked to two or more oligomers which may independently be the same or different and which may independently be straight chain or branched and one or more identifiers attached to the solid support which define the molecular structure of the oligomers of the synthetic receptor, the method comprising the steps of:

a) coupling a protected polyfunctional organic template to a solid support;

b) reacting the protected polyfunctional organic template with an activator to remove the protecting group thereby exposing the active site;

c) coupling a protected oligomer monomer to the deprotected polyfunctional organic template;

d) coupling an identifier to the solid support; and e) repeating steps (b) through (d) from one to twenty times for each oligomer of the synthetic receptor.

The invention also provides a method of preparing a synthetic receptor library with identifiers comprising a plurality of different synthetic receptor members, wherein each synthetic receptor library member comprises a solid support having attached thereto a single type of synthetic receptor which comprises a polyfunctional organic template covalently linked to two or more oligomers which may be independently the same or different and which may independently be straight chain or branched and one or more identifiers which define the synthetic receptor, the method comprising the steps of:

a) apportioning the solid supports among a plurality of reaction vessels;

b) reacting the solid supports in each reaction vessel with a first oligomer monomer;

c) reacting the solid supports in each reaction vessel with a first identifier;

d) pooling the solid supports;

e) apportioning the pooled supports among a plurality of reaction vessels;

f) reacting solid supports in each reaction vessel with a second oligomer monomer;

g) reacting the pooled solid supports in each reaction vessel with a second identifier;

h) repeating steps (d) through (g) from at least one to twenty times for each oligomer; and i) reacting the solid supports in each reaction vessel with a polyfunctional organic template.

A method of preparing a synthetic receptor with one or more identifiers which comprises a polyfunctional organic template covalently linked to two or more oligomers which may independently be the same or different and which may independently be straight chain or branched and one or more identifiers attached to the solid support which define the molecular structure of the oligomers of the synthetic receptor, the method comprising the steps of:

a) prepare a multifunctional solid support containing a active sites blocked with protecting groups;

b) reacting the solid support with an activator to remove a first type of protecting group thereby exposing a first type of active site;

c) coupling a protected oligomer monomer to the first type of active site of the solid support;

d) react the solid support with an activator to remove a second type of protecting group thereby exposing a second type of active site;

e) coupling a protected identifier to the second type of active site; and f) repeating steps (b) through (e) from one to twenty times for each oligomer;

g) reacting the protected oligomer on the solid support with an activator to remove the protecting group thereby exposing an active site;

h) coupling a polyfunctional organic template to the active site.

In the methods described above the identifier is a stable chemical molecule or a plurality of stable chemical molecules distinguishable and detectable to picomolar levels or an oligonucleotide. The solid supports coupled to the polyfunctional organic templates in each reaction vessel may first be reacted with an identifier and then the polyfunctional organic templates on the solid supports may be reacted with an oligomer monomer.

The invention also provides a method for assaying a synthetic receptor library to determine a suitable synthetic receptor for an acceptor molecule of interest, the method comprising the steps:

a) generating a synthetic receptor library;

b) contacting the synthetic receptor library with the acceptor molecule of interest under conditions such that the acceptor molecule interacts and binds to one or more suitable synthetic receptors of the synthetic receptor library;

c) isolating the suitable synthetic receptor(s) that exhibit binding to the acceptor molecule; and d) determining the molecular structure of the suitable synthetic receptor(s).

The acceptor molecule introduced for the assay may be linked to a label. The label attached to the acceptor molecule introduced identifies the suitable synthetic receptor(s) interacting with the acceptor molecule. The label may be a dye, a fluorescent label or a radioactive label.

The acceptor molecule of interest may be selected from the following, an antibody, a peptide, a protein, a carbohydrate, a nucleic acid, a lipid, a drug, a metal or a small molecule. In the case of a peptide receptor, the peptide may be an adrenocorticotropic hormone and fragments, angiotensin, atrial natriuretic, bradykininin, chemotatic, dynorphin, endorphins and beta-lipotropin fragments, enkephalin, enzyme inhibitors, fibronectin fragments, gastrointestinal, growth hormone releasing peptides, luteinizing hormone releasing peptide, melanocyte stimulating hormone, neurotensin, opioid, oxytocin, vasopressin, vasotocin, parathyroid hormone and fragments, protein kinase, somatostatin, substance P. In the case where the protein acceptor molecule is a growth hormone it may be selected from the group comprising human, bovine, porcine, avian, ovine, piscine, or equine growth hormone, and polypeptide analogs thereof having the biological activity of the corresponding naturally occurring growth hormone. In addition, the protein which is a growth factor may be IL-1, IL-2, IL-3, IL-4, IL-5, IL-6, IL-7, IL-8, IL-9, IL-10, IL-11, IL-12, IL-13, IL14, EGF, aFGF, bFGF, TGF-beta1, TGF-beta2, TGF-beta3, G-CSF, GM-CSF, M-CSF, EGF, IGF-I, IFN, IL, LIF, KGF, OSM, PDGF, TNF, cytokines, kit ligand, EPO, transforming growth factor, nerve growth factor, brain derived growth factor, neurotrophin-3, neurotrophin-4, heptaocyte growth factor. The protein may also be a receptor for any of the above peptides, or growth factors. The acceptor molecule may also be present on whole cells, viruses or bacteria. Other acceptor molecules include molecules on a cancer cell associated with the following cancers, melanoma, lip, tongue, mouth, pharynx, esophagus, stomach, small intestine, colon, rectal, liver, pancreas, larynx, lung, bone, connective tissue, skin, breast, uterus, ovary, prostate, testis, bladder, kidney, eye, brain, central nervous system, endocrine glands, blood and lymph tissues or leukemia. The invention is also directed to a synthetic receptor selectively binding an acceptor molecule in the presence of other different acceptor molecules.

The invention further provides a method for assaying a synthetic receptor library for suitable synthetic receptor(s) that exhibit biological activity, the method comprising the steps of:

a) generating a synthetic receptor library;
b) detecting the biological activity of suitable synthetic receptors of the synthetic receptor library in situ;
c) isolating the suitable synthetic receptor(s) that exhibit the biological activity; and
d) determining the molecular structure of the suitable synthetic receptor(s) isolated in step (c).

The biological activity of interest is e.g., cytotoxicity, antitumor activity, antibacterial activity, antiviral activity, antifungal activity, anti-parasite activity, growth factor activity, growth inhibitory activity, hormone activity, neurotransmitter activity, immunomodulator activity, regulatory activity or enzymatic activity. In the assays described above the activity of interest is determined at nanomolar concentrations and the synthetic receptor(s) detected may be of use as a therapeutic agents or as a diagnostic agents. Furthermore, a suitable synthetic receptor may selectively bind to a transition state analogue.

Another embodiment of the invention includes a method for assaying a synthetic receptor library for a suitable synthetic receptor(s) which catalyzes a reaction, the method comprising the steps of:

a) generating a synthetic receptor library;
b) introducing to the synthetic receptor library a substrate such that an catalyzed reaction product is determined;
c) isolating the suitable synthetic receptor(s) that exhibits catalytic activity; and
d) determining the molecular structure the suitable synthetic receptor(s) isolated in step (c).

In addition, the invention provides a method for assaying a synthetic receptor library for a suitable synthetic receptor (s) which inhibits an enzyme-catalyzed reaction, the method comprising the steps of:

a) generating a synthetic receptor library;
b) introducing to the synthetic receptor library an enzyme that catalyzes a reaction of interest in situ;
c) detecting inhibition by a suitable synthetic receptor(s) of the enzymecatalyzed reaction of interest in situ;
d) isolating the suitable synthetic receptor(s) that exhibits inhibition of enzyme catalyzed reaction of interest in situ; and e) determining the molecular structure the suitable synthetic receptor(s) isolated in step (c).

This invention will also be directed to the use of the receptors to detect a drug and in the detection of an illicit drug, i.e., a narcotic, an antabolic steroid.

This invention includes a method for creating new synthetic receptors and libraries of synthetic receptors which can mimic monoclonal antibodies has been developed.

The synthetic receptor molecules herein, may selectively bind almost any desired substrate. Using combinatorial synthesis large libraries of synthetic receptors can be generated. Once prepared the libraries of synthetic receptors can be used to screen for synthetic receptor members that have a desired characteristic. A library of synthetic receptors is synthesized using combinatorial techniques. The synthetic receptor library may be prepared by any of the known methods for combinatorial synthesis (G. Jung and A. G. Beck-Sickinger, *Angew. Chem. Int. Ed. Engl.* 1992, 367–383, 31; M. R. Pavia, T. K. Sawyer and W. H. Moos, *Bioorg. Med. Chem. Lett.*, 1993, 387–396, 3).

The synthetic receptors members have the following general formula (Scheme 1):

Scheme 1
General formula for synthetic receptor members.

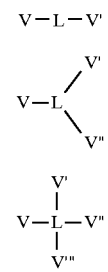

where L is a polyfunctional organic template which is chemically bonded to V, V', etc. which are oligomers. Scheme 1 is a subset of the general formula L—(—V$^N$)$_M$. A synthetic receptor library will consist of a collection of such synthetic receptor molecules (i.e. a library) having a variety of different oligomers V, V', etc. groups. In some cases it will be desirable to attach the polyfunctional organic template to a solid support particle (P) as diagrammed below such that any given solid support particle has only one type of synthetic receptor (i.e. one type of synthetic receptor member of the library) bound to it.

Scheme 2
Solid support particle attached to a synthetic receptor molecule.

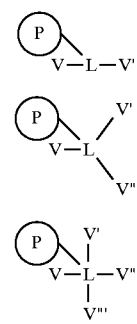

A substrate of interest, detectable at nanomolar levels by way of its color, its fluorescence, its radioactivity, etc., may be prepared, such detectable substrates are referred to as labeled substrates.

The synthetic receptor library is then assayed to find those members of the library which have the desired interaction with the labeled substrate. In the case where the desired interaction is binding to the substrate, the synthetic receptor library is mixed with a solution of the labeled substrate and those library members that bind to the labeled substrate are selected. This procedure is particularly simple when the synthetic receptor library members are bound to a solid support as shown in Scheme 2. In that case, solid support particles having receptors which bind the labeled substrate accumulate color or fluorescence or radioactivity (depending on the nature of the label used). Depending on the concentration of the labeled substrate used, the assay can be adjusted to detect binding of any desired strength: for example, if the amount of labeled substrate in the presence of the receptor library is adjusted to give a 100 $\mu$M concentration of free (unbound) labeled substrate, then assay will only detect template-substrate binding with association constants (k) of $(100\ \mu M)^{-1}$ or greater.

In the case where the desired interaction is catalysis of a chemical reaction, the synthetic receptor library is mixed with a solution of the labeled substrate and those library members are selected which catalyze the conversion of the substrate to a reaction product. Detection of reaction products for synthetic receptor library members having catalytic activity may be determined for example by HPLC (high performance liquid chromatography) analysis. The synthetic receptors showing catalytic activity are then isolated from the library.

Once the desired synthetic receptor library member(s) is selected using the assay as described above, then the structure of the synthetic receptor(s) is determined.

The templates (L) will desirably have limited conformational mobility and functionality oriented in such a way that the variable oligomeric chains are directed toward nearby regions of space. Some selected examples of such suitable templates include polyfunctional steroids such as steroidal diols, triols and macrocyclic templates as shown below. The oligomeric chains are indicated by V or V'. In these figures, R represents any stable organic functionality (and is unimportant to the properties of the template) in the case of the free template library while R represents a functional group with a connection to a solid support (e.g. —CONH-polymer) in the case of the solid phase supported library.

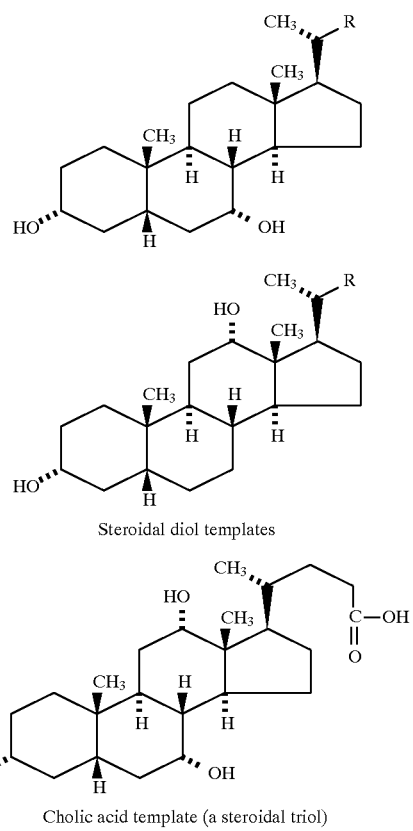

Steroidal diol templates

Cholic acid template (a steroidal triol)

Cholic acid could form the basis for a triple chained template (this is an example of the LVV'V" described above). In the cholic acid-based templates described above, the D-ring side chain served as a convenient appendage with which to bind the template to a solid support. With other templates, such an appendage may be absent but may be inserted by adding a trifunctional material to one of the template functional groups. This material would provide two remaining groups which could be used for attaching the solid support (R) and the variable oligomer (V, V', etc).

The effect of having a rigid polyfunctional organic template is well illustrated by the binding observed for Leu Enkephalin shown below. In the case of the peptidsteroidal receptor library has an estimate 300 sequences binding Leu Enkaphalin, with a $K_{D\text{-}Max}=75–85\ \mu M$

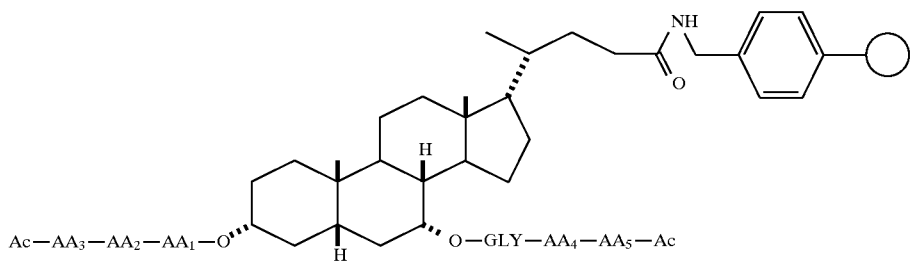

Figure 2:
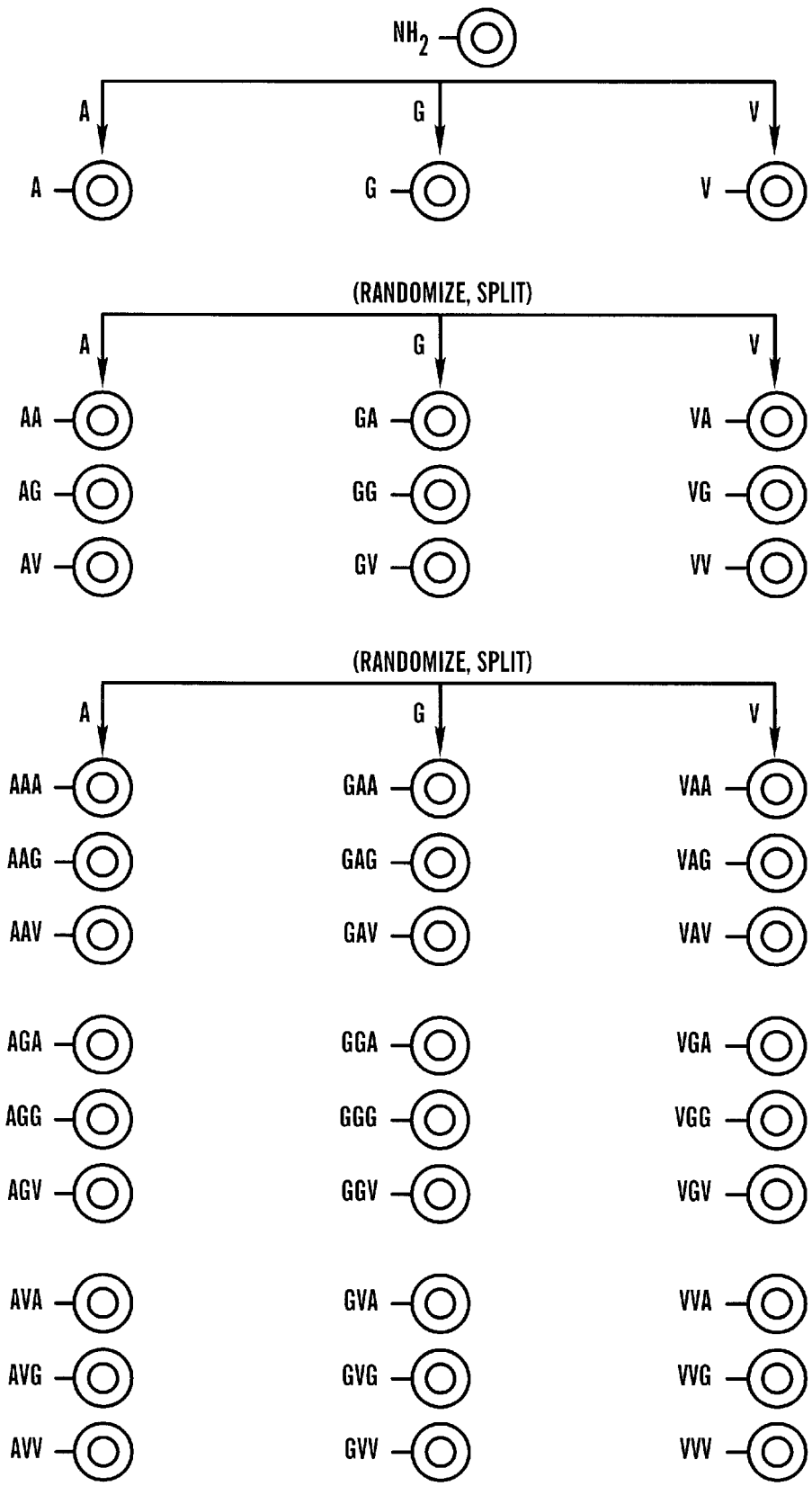
FIG. 2.

However, in the less rigid example shown below, has a estimate 2000 sequences bind Leu Enkaphalin, KD-Max= 200 μM.

sequences. The "one-bead, one-oligomer sequence" concept can be achieved easily by separating and mixing beads during the synthesis. FIG. 2 demonstrates the synthesis of 27

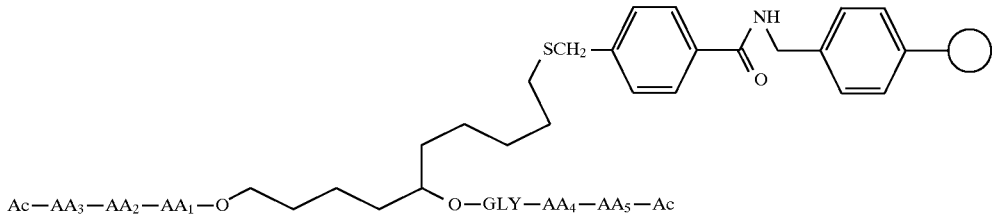

A variety of nonsteroidal templates could also be used to produce synthetic receptor libraries based, for example, on macrocyclic liner cores as shown below. This structure is generally based on a known template (Yoon and Still, *J. Am. Chem. Soc.*, 115, 823, 1993). In general, templates can include any di-, tri- or tetra-, etc. functionalized organic structure where the functionality allows attachment of the variable oligomeric chains (V, V', etc).

For the variable oligomeric chains (V, V', etc), any oligomer can be used. Thus V, V', etc can consist of oligoamides, oligoesters, oligoureas, oligourethanes, oligoamines, oligoethers, oligosulfonamides, oligophosphonamides, oligophosphonates, oligophosphates, etc. as well as mixed oligomers composed of mixtures of the foregoing functionalities. The chain can be either linear or branched and can incorporate both cyclic and acyclic segments. Branched oligomers will be utilized to generate larger binding sites which should give tighter and more selective substrate binding. oligomers composed of conformationally rigid fragments or segments are of interest because they help preorganize the template and therefore increase its selectivity. In a preferred embodiment the oligomers are polypetides, oligonucleotides or a mixture thereof.

As discussed, combinatorial synthesis is a convenient method to generate a receptor library containing a diverse and numerous number of molecules. These combinatorial synthetic techniques include, multi-pin method (Geysen, H. M.; Meloen, R. and Barteling, S. *Proc. Natl. Acad. Sci. USA*, 1984, 81, 3998; Geysen et al., *Proc. Natl. Acad. Sci. U.S.A.*, 1985, 82, 178; WO 84/03564; WO 86/06487; PCT/AU85/00165 (WO 86/00991), U.S. Pat. No. 5,133,866), tea-bag method (U.S. Pat. No. 4,631,211; Houghton et al., *Int. J. Peptide Protein Res.*, 1986, 27, 673; Houghton et al., *Biotechniques*, 1986, 4, 6, 522; Houghten, R. A. *Proc. Natl. Acad. Sci. USA*, 1985, 82, 5131; WO 92/09300; WO 92/09300), cellulose-paper method (Frank, R. and Doering, R. *Tetrahedron Lett*. 1988, 44, 6031), light-directed method (also termed as VLSIPS method, Fodor, S. P. A.; Read, J. L.; Pirrung, M. C.; Stryer, L.; Lu, A. T. and Solas, D. *Science* 1991, 251, 767,; U.S. Pat. No. 5,143,854; WO 90/15070; WO 92/10092) and the split-synthesis method (Lam, K.; Salvon, S.; Hersh, E.; Hruby, V.; Kazmierski, W. and Knapp, R. *Nature*, 1991, 354, 82; WO 92/00091, WO 93/06121). However, the split-synthesis method is superior to the other methods as it offers a procedure involving the systematic synthesis and screening of oligomer libraries of defined structure. The procedure for split synthesis involves creating a large oligomer library consisting of thousands to billions of different molecules. The molecules may be attached to particles such as beads, with each bead containing a single oligomer sequence and with the collection representing numerous combinations of possible random oligomer sequences tripeptides comprising alanine (A), glycine (G) and valine (V) by the split-synthesis method. At the end of the synthesis, each bead has only one product from a specific reaction sequence.

Since the amount of products on each bead is normally 50–200 pmol, the structure elucidation of such small amount of products restricts the split-synthesis method to the synthesis of nucleotides or peptides composed of natural amino acids. The split-synthesis method alone fails to provide access to other libraries comprising unnatural monomers.

In order to solve the structure elucidation problem, readable tags (oligonucleotide tag or peptide tag) are co synthesized to encode the series of steps and reagents used in the synthesis of each library element (Berner, S. and Lerner, R. A. *Proc. Natl. Acad. Sci, USA*, 1992, 89, 5381; Kerr, J. M.; Banville, S. C. and Zuckermann, R. N. *J. Am. Chem. Soc.* 1993, 115, 2529). Once a library element is selected by certain assay, its structure can be identified by sequencing its peptide tag or oligonucleotide tag after PCR amplification. The main problem with the above encoding methods is the at the tagging structures are chemically liable and destroyed by many of the reagents and conditions normally associated with the synthetic organic chemistry. Furthermore, the oligonucleotide or peptide tags may themselves associate with biological receptors and confuse binding or enzymatic assays. Recently, an alternative encoding method was developed using molecular tags (M. J. H. Ohlmeyer, R. N. Swanson, L. W. Dillard, J. C. Reader, G. Asouline, R. Kobayashi, M. Wigler and W. C. Still, (1993) *Proc. Natl. Acad. Sci. USA*, 90, 10922–10926). This technique makes use of highly sensitive, chemically inert molecular tags and a binary encoding scheme. This method provides a practical solution for the construction of large, chemically diverse libraries.

The binary encoding scheme allows the encoding of the maximum amount of information by using the minimum number of tag molecules. For example, a simple combinatorial synthesis using any of 7 different reagents in each step is carried out. These seven different reagents can be designated by three tag molecules through the binary encoding scheme as tag 1 for reagent, tag 2 for reagent 2, tag 1 and tag 2 for reagent 3, . . . , tag 1, tag 2 and tag 3 for reagent 7. This letter description can be simply translated into binary numerical description as 001 (reagent 1), 010 (reagent 2), 011 (reagent 3), . . . , 111 (reagent 7). The binary encoding scheme only requires 3N tag molecules to encode $7^N$ different final products in the library, where N is the number of chemical steps for synthesis of the library.

The tag molecules used are shown below.

Scheme 3
The structures of tagging molecules

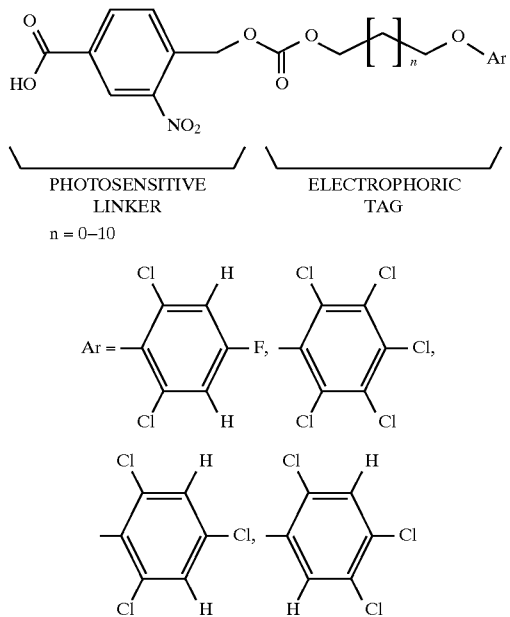

The molecular tags are varied by different lengths of the hydrocarbon (n=0–10) and three different electrophores (Ar). With a photocleavable linker (Patchornik, A.; Amit, B. and Woodward, R. B. *J. Am. Chem. Soc.* 1970, 92, 6333), the electrophoric tags can be easily liberated from solid-supports by irradiation with light of wavelength longer than 320 nm. The liberated alcohols are then silylated by N,O-bis (trimethylsilyl) acetamide in N,N-Dimethylformamide. The resulting silyl ethers are well separated by capillary GC and selectively detected by EC electron capture) at levels <1 pmol. More than 20 tagging molecules were prepared which allow encoding of up to $2^{20}$ different synthesis. Using the above binary encoding scheme and tagging molecules, two different receptor libraries composed of 10,000–20,000 receptor members have been prepared. Through color screening with a labeled substrate (vide infra), it was possible to select several synthetic receptor molecules from the libraries as the mimics of the antibody against Enkephalin i.e., "synthetic antibodies", which is conceptually represent below.

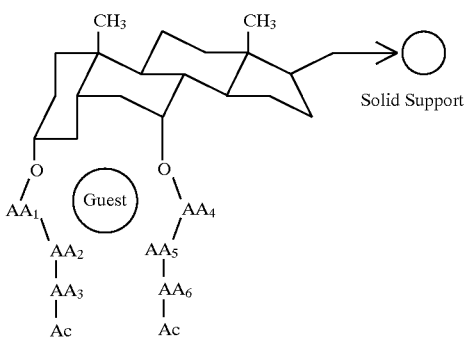

A binding constant with free energy of formation ΔG to the acceptor of 5 Kcal/mol to 12 Kcal/mol is desirable, in some cases the preferred free energy of formation ΔG may be 9 Kcal/mol to 12 Kcal/mol and in other cases a ΔG of 8 Kcal/mol to 15 Kcal/mol is desirable.

The following experimental details are set forth to aid in an understanding of the invention, and are not intended, and should not be construed, to limit in any way the invention set forth in the claims which follow thereafter.

EXAMPLE 1

General Procedures

All the reactions on solid support were carried out in Merrifield reaction vessels. The reaction vessels were silylated by the treatment of 10% Trimethylsilylchloride in toluene at room temperature for 1 hour followed by washing and drying prior to use. A Burrell Wrist Action Shaker was used to shake reaction vessels. Anhydrous solvents were used for reaction, which were either distilled or purchased from Aldrich Inc. Solvents used for washing beads were reagent grade. Photolysis of beads was carried out in MeOH or N,N-Dimethylformamide by irradiating beads under UV light with a Model UVL-56 (UVP, Inc., San Gabriel, Calif.) Ultraviolet lamp at 366 nm. Aminomethyl resin was purchased from Balchem, Inc. (200–400 mesh, 0.6 mmol/g) or Sigma, Inc. (100–200 mesh, 1.1 mmol/g[18]).

The tag molecules used for encoding the synthesis of the libraries are shown in Scheme 3. They are simply named as $C_n$, 2,4,5 $Cl_3$; $C_n$, 2,4,6 $Cl_3$ and $C_n$, $Cl_5$ stand for 2,4,5 trichloro phenyl, 2,4,6, trichloro phenyl and pentachloro phenyl groups respectively.

Amino acids used for the synthesis of the following libraries were Alanine, Valine, Leucine, Phenylalanine, Proline, Serine, Threonine, Lysine, Aspartic acid and Glutamic acid. Alanine, Valine, Leucine, Phenylalanine and Proline are 9-Fluorenylmethyloxycarbonyl for α-amino group and t-butyl for side-chain protection. Lysine is protected by 9-Fluorenylmethyloxycarbonyl for α-amino group and tert-Buthyloxycarbonyl for ζ-amino group.

Figure 3:
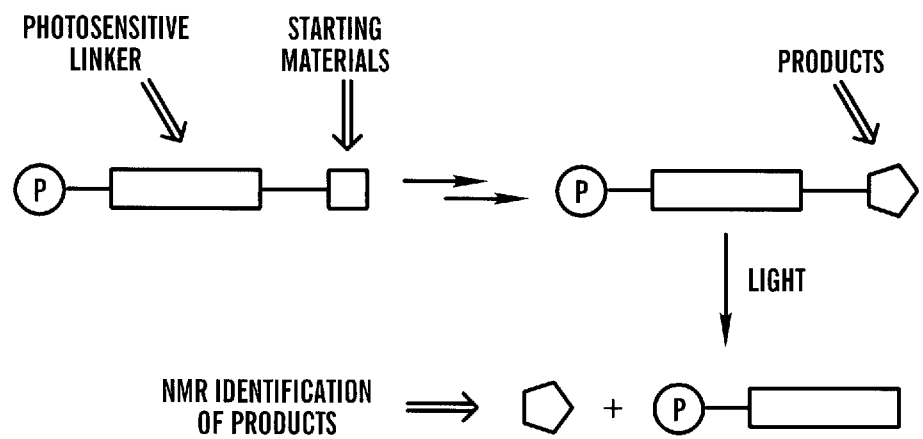
FIG. 3.

During the solution synthesis, the progress of reactions can be easily monitored by checking TLC of reaction mixtures. However, almost no reactions except peptide formation can be monitored during the solid-phase synthesis. Solid-phase synthesis normally requires the use of a large excess of reactants and multiple couplings to convert starting materials to products. It is therefore much more difficult to do selective functionalization on a solid-phase support than in solution due to the lack of detecting tools for monitoring reactions and the necessity of using large excess reactants during the synthesis. In order to monitor the reactions other than peptide formation on solid supports, a "detectable solid phase synthesis" method was developed which is shown in FIG. 3.

By introducing a photosensitive linker between the template and solid support, reactions can be monitored by nuclear magnetic resonance (spectroscopy) of the free products liberated from beads by photolysis, the synthesis of detectable beads is described below.

The Gly-library was constructed on aminomethyl resin (200–400 mesh, 0.6 mmol/g) which was purchased from Bachem, Inc.

The Pro-library was constructed on aminomethyl resin (100–200 mesh, 0.9 mmol/g) which was purchased from Sigma, Inc.

| LIST OF ABBREVIATIONS | |
|---|---|
| AA | Amino Acid |
| Ac | Acetyl |
| $Ac_2O$ | Acetic anhydride |
| Ala | Alanine |

LIST OF ABBREVIATIONS -continued

| | |
|---|---|
| aq. | Aqueous |
| Asp | Aspartic acid |
| atm. | Atmosphere |
| 9-BBN | 9-Borabicyclo[3.3.1]nonane |
| Boc | tert-Butyloxycarbonyl |
| n-Bu | n-Butyl |
| t-Bu | tert-Butyl |
| cat. | Catalytic amount |
| CSA | Camphorsulfonic acid |
| DCC | Dicyclohexylcarbodiimide |
| DET | Diethyl tartrate |
| DIAD | Diisopropyl azodicarboxylate |
| DIBAH | Diisobutylaluminum hydride |
| DIPEA | Diisopropylethyl amine |
| DIPT | Diisopropyl tartrate |
| DMAP | 4-Dimethyiaminopyridine |
| DMF | N,N-Dimethylformamide |
| DMSO | Dimethyl sulfoxide |
| EC | Electron capture (detector) |
| EDC | N-Ethyl-N'-(3-dimethylaminopropyl)carbodiimide |
| ee | Enantiomeric excess |
| eq. | Equivalent |
| Et | Ethyl |
| EtOAc | Ethyl acetate |
| EtOH | Ethanol |
| FMOC | 9-Fluorenylmethyloxycarbonyl |
| GC | Gas Chromatography |
| Glu | Glutamic acid |
| h | Hour or hours |
| HOAC | Acetic acid |
| HOBT | 1-hydroxybenzotriazole |
| HMPA | Hexamethylphosphoric triamide |
| hv | Light |
| i-Pr | Isopropyl |
| i-PrOH | 2-Propanol |
| LAH | Lithium aluminum hydride |
| LDA | Lithium diisopropylamide |
| Leu | Leucine |
| Lys | Lysine |
| MCPBA | m-Chloroperoxybenzoic acid |
| Me | Methyl |
| MeOH | Methanol |
| MeCN | Acetonitrile |
| mol | MOLE |
| mp | Melting Point |
| Ms | Mesyl(methanesulfonyl) |
| NMO | N-Methylmorpholine N-oxide |
| NMR | Nuclear magnetic resonance (spectroscopy) |
| --P | Amino methyl resin support |
| Ph | Phenyl |
| Phe | Phenylalanine |
| Pro | Proline |
| Py | Pyridine |
| r.t. | Room temperature |
| TBDMS | tert-Butyldimethylsilyl |
| TEA | Triethyl amine |
| TFA | Trifluoroacetic acid |
| THF | Tetrahydrofuran |
| THP | Tetrahydropyran |
| Thr | Threonine |
| TLC | Thin layer chromatography |
| TMS | Trimethylsilyl |
| Ser | Serine |
| Val | Valine |
| uv | Ultraviolet (spectroscopy) |

The Synthesis of Detectable Beads

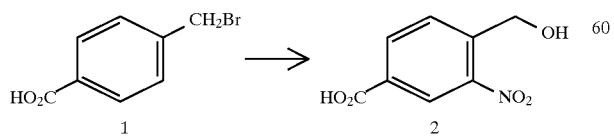

α-Bromo-p-toluic acid (21.5 g, 100 mmol) was added in five equal portions to 90% $HNO_3$ (250 mL) at −10° C. The reaction mixtures were stirred at −10° C. for 3 h and poured into ice-water. After stirring at room temperature for 3 h, the white precipitate was filtered, collected and dried by air overnight to give ortho-nitro a-bromo-ptoluic acid (22.2 g, 85%) as slightly yellow solid.

To the potassium carbonate aqueous solution (35.0 g, 200 mL $H_2O$) was added ortho-nitro a-bromo p-toluic acid (13.1 g, 50 mmol). The homogenous solution was stirred at room temperature overnight and then cooled at 0° C. Concentrated HCl was added until PH=1. The resulting white precipitate was filtered, collected and dried in air to afford 2 as white solid (8.9 g, 95% mmol). The filtrate was extracted with ethyl acetate three times. The combined extracts were washed with brine, dried over $MgSO_4$, filtered and concentrated to give another portion of 2 as slightly yellow solid (1.0 g, 5%).

$^1$H NMR ($CD_3OD$) 4.98 (s, 2H), 7.96 (d, 1H, J=8.12 Hz), 8.25 (dd, 1H, J=1.72, 8.16 Hz), 8.56 (d, 1H, J=1.64 Hz).

$^{13}$C NMR ($CD_3OD$) 61.85, 126.56, 129.70, 131.96, 135.11, 143.94, 148.29, 167.39.

IR (KBr) 3450, 2953, 1726, 1152, 1080 $cm^{-1}$.

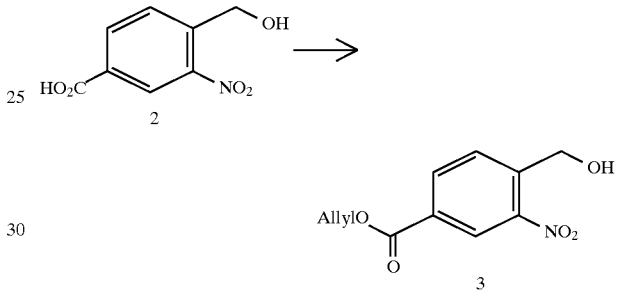

To the ortho nitro α-hydroxy p-toluic acid (9.9 g, 50 mmol) in allyl alcohol (200 mL) was added p-TsOH $H_2O$ (850 mg, 5 mmol). The mixtures were under flux for 24 h and concentrated to dryness. The resulting residue was then dissolved in 500 mL ethyl acetate, washed with saturated sodium bicarbonate solution and dried over $MgSO_4$. Removal of ethyl acetate and recrystalization from MeOH to give the allyl ester 3 as a slightly yellow solid (9.3 g, 95%).

$^1$H NMR ($CDCl_3$) 2.61 (bs. 1H), 4.86 (dt, 2H, J=5.84, 1.40 Hz), 5.07 (s, 2H), 5.33 (dd, 1H, J=10.4, 1.28 Hz), 5.43 (dd, 1H, J=17.24, 1.48 Hz), 6.21 (ddt, 1H, J=5.76, 10.44, 17.24 Hz), 7.92 (d, 1H. J=8.08 Hz), 8.31 (dd, 1H, J=1.64, 8.08 Hz), 8.72 (d, 1H, J=1.60 Hz).

$^{13}$C NMR ($CDCl_3$) 61.94, 66.30, 118.99, 125.89, 129.49, 130.67, 131.58, 134.27, 141.54, 147.66, 164.04.

IR (KBr) 3500, 3089, 2946, 1726, 1649, 1622, 1537, 1492, 1406, 1281, 1253, 1189, 1151, 1125, 1080, 1049, 974, 853, 832, 774 $cm^{-1}$.

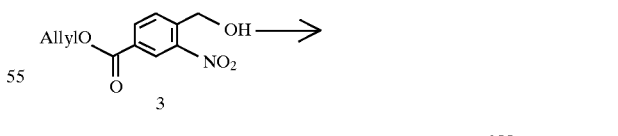

To a solution of chenodeoxycholic acid (3.94 g, 10 mmol) and ortho nitro α-hydroxy p-toluic acid (2.4 g, 10 mmol) in CH₂Cl₂ (50 ml) was added N-Ethyl-N'-(3-dimethylaminopropyl)carbodiimide (2.9 g, 15 mmol) and 4-Dimethylaminopyridine (120 mg, 1 mmol). The reaction mixture was stirred at room temperature for 2 hours. After which time the reaction mixture was diluted with 200 mL ethyl acetate, washed with 1N HCl twice and brine once, dried over MgSO₄ and concentrated in vacuo. The crude product was subjected to flash chromatography to yield the desired product 4 as a white foam solid (5.3 g, 87%, R$_f$=0.75, 25% hexanes in EtOAc)

¹H NMR (CDCl₃ 0.65 (s, 3H), 0.89 (s, 3H), 0.94 (d, 3H, J=6.24 Hz), 0.96–2.05 (m, 25 H), 2.19 (dt. 1H, J=12.8, 12.8 Hz), 2.35 (m, 1H), 2.47 (m, 1H), 3.45 (m, 1H), 3.84 (m, 1H), 4.86 (d, 2H, J=5.76 Hz), 5.33 (d, 1H, J=10.36 Hz), 5.42 (dd, 1H, J=17.16, 1.28 Hz), 5.55 (s, 2H), 6.03 (ddt, 1H, J=5.76, 10.52, 17.12 Hz), 7.69 (d, 1H, J=8.12 Hz), 8.30 (dd, 1 H, J=1.6, 8.12 Hz), 8.74 (d, 1H, J=1.6 Hz). ¹³C NMR (CDCl₃) 11.77, 18.27, 20.62, 2.74, 23.67. 28.09, 30.75, 30.94, 31.02, 32.94, 34.76, 35.07, 35.29, 35.40, 39.53, 39.71, 39.96, 41.60, 42.73, 50.50, 55.86, 62.38, 66.35, 68.43, 71.95, 119.07, 126.01, 129.20, 131.19, 131.56, 134.01, 136.83, 147.84, 163.80, 173.22.

IR (KBr) 3500, 3089, 2945, 1726, 1649, 1622, 1537, 1492, 1406, 1348, 1151, 1080, 1049, 974, 743 cm⁻¹

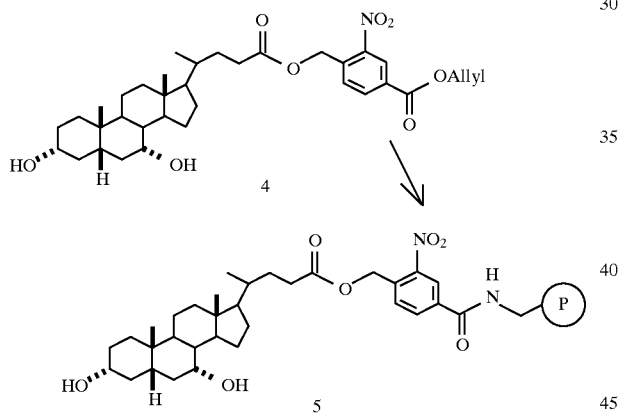

The allyl ester 4 (3.0 g, 4.9 mmol) and Pd(PPh₃)₄ (115 mg. 0.1 mmol) in 15 mL CH₂Cl₂ was cooled to 0° C. Pyrrolidine (840 μL, 10 mmol) in 2 mL CH₂Cl₂ was added dropwise. The reaction mixtures were stirred at 0° C. for 45 min, and then EtOAc (200 mL) and 1N HCl (50 mL) were added. The organic layer was washed with brine, dried over MgSO₄, filtered and concentrated to afford the free acid as a slightly yellow solid.

To the pre-swelled aminomethyl resin (3.0 g, 0.6 mmol/g) in a 50 mL reaction vessel were added the above free acid 1-hydroxybenzotriazole (675 mg, 5 mmol) and DIC (660 μL, 4.5 mmol) in 30 mL DMF. The reaction mixtures were shaken at room temperature for 6–8 h until the Kaiser test indicated the completion of the reaction. The reagents were filtered, and beads were washed with 3×N,N-Dimethylformamide, 3×i-PrOH and 5×CH₂Cl₂, and then dried to give the detectable beads 5 (4.0 g).

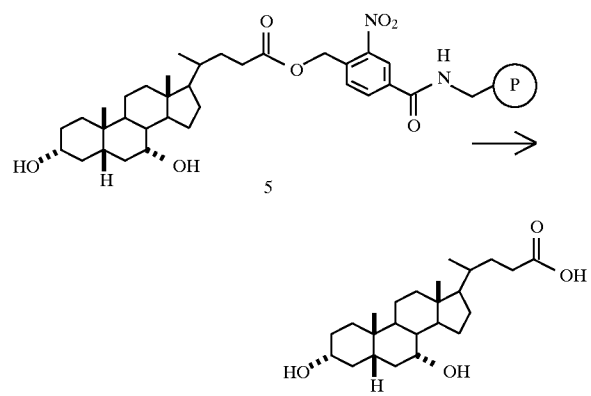

The above beads (5) (40 mg) and 500 μL CH₃OH in a capped 1 mL test tube under Ultraviolet light for 12 hours at room temperature. The beads were filtered, and the filtrate was concentrated to give a white solid whose NMR spectrum indicated that only chenodeoxycholic acid was formed.

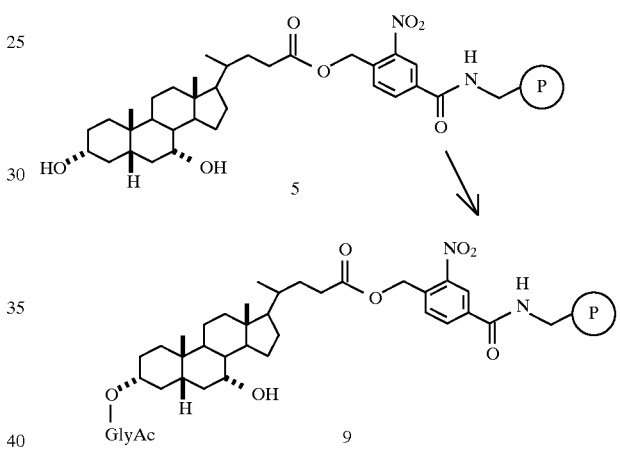

To the detectable beads 5 (200 mg, 0.9 mmol) was added diisopropylethyl amine (110 μL, 0.6 mmol) in 1 mL N,N-dimethylformamide followed by the addition of 9-fluorenylmethyloxycarbonyl-GlyF (135 mg, 0.45 mmol) in 1 mL N,N-dimethylformamide. After shaking at room temperature for 3 hours, reagents were filtered and the beads were washed with N,N-dimethylformamide (5 mL) once. The resulting beads were retreated with diisopropylethyl amine and 9-fluorenylmethyloxycarbonyl-GlyF in N,N-dimethylformamide twice under the same conditions and then washed with 3×N,N-dimethylformamide to give C₃-OGly-9-fluorenylmethyloxycarbonyl, C₇—OH beads.

To the above beads was added 1:1 N,N-dimethylformamide/piperidine (5 mL). The reaction vessel was shaken at room temperature for 30 min, and then the beads were washed with 4×N,N-dimethylformamide followed by the treatment of HOAc (27 μL, 0.45 mmol), 1-hydroxybenzotriazole (68 mg, 0.5 mmol) and DIC (70 μL, 0.45 mmol) in 2 mL N,N-dimethylformamide. The reaction mixtures were under shaking for 2 hours until the Kaiser test indicated the completion of the reaction. The beads were then thoroughly washed with 2×N,N-dimethyformamide (5 mL, 2 min each), 3×i-PrOH (5 mL, 2 min each) and 5×CH₂Cl₂ (5 mL, 2 min each), and then dried on pump to afford beads 9.

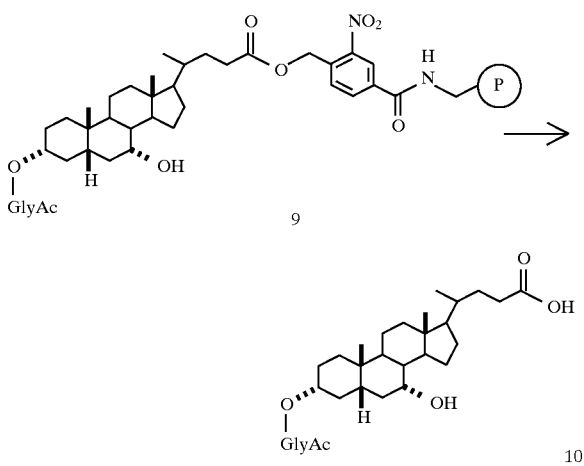

The resulting beads 9 (40–50 mg) and 500 μL N,N-dimethylformamide in a capped 1 mL test tube were under Ultraviolet light for 12 hours. The beads were filtered, and the filtrate was concentrated to give 10 as a white solid. The NMR spectrum of 10 indicates that the selectivity for esterification of $C_3$—OH and $C_7$—OH is 19:1.

The above beads were again treated with 1:1 N,N-Dimethylformamide/piperidine (5 mL) to remove the 9-Fluorenylmethyloxycarbonyl-protecting group. The reaction vessel was shaken at room temperature for 30 min, and the beads were washed with 4×N,N-dimethyformamide, and the treated with 9-Fluorenylmethyloxycarbonyl-Phenylalanine (97 mg, 0.25 mmol), 1-hydroxybenzotriazole (35 mg, 0.25 mmol) and DIC (40 μl, 0.25 mmol) in 2 mL N,N-dimethylformamide. The reaction mixtures were under shaking for 3 hours until the Kaiser test indicated the completion of the reaction. The beads were then thoroughly washed with 2×N,N-dimethyformamide (5 mL, 2 min each) and 5×$CH_2Cl_2$ (5 mL, 2 min each) to give the $C_3$-OGlyPhenylalanine-9-Fluorenylmethyloxycarbonyl, $C_7$—OH beads.

To the above beads was added 1:1 N,N-dimethyformamide/piperidine (5 mL). After under shaking at room temperature for 30 min, the beads were washed with 4×N,N-dimethylformamide and treated with HOAc (27 μL, 0.45 mmol), 1-hydroxybenzotriazole (35 mg, 0.25 mmol) and DIC (70 μL, 0.45 mmol) in 2 mL N,N-dimethylformamide. The reaction mixtures were under shaking for 2 h until the Kaiser test indicated the completion of the reaction.

The beads were then thoroughly washed with 2×N,N-dimethyformamide (5 mL, 2 min each) and 5×$CH_2Cl_2$ (5 mL, 2 min each) to give the $C_3$-OGlyPhenylalanineAc,$C_7$—OH beads.

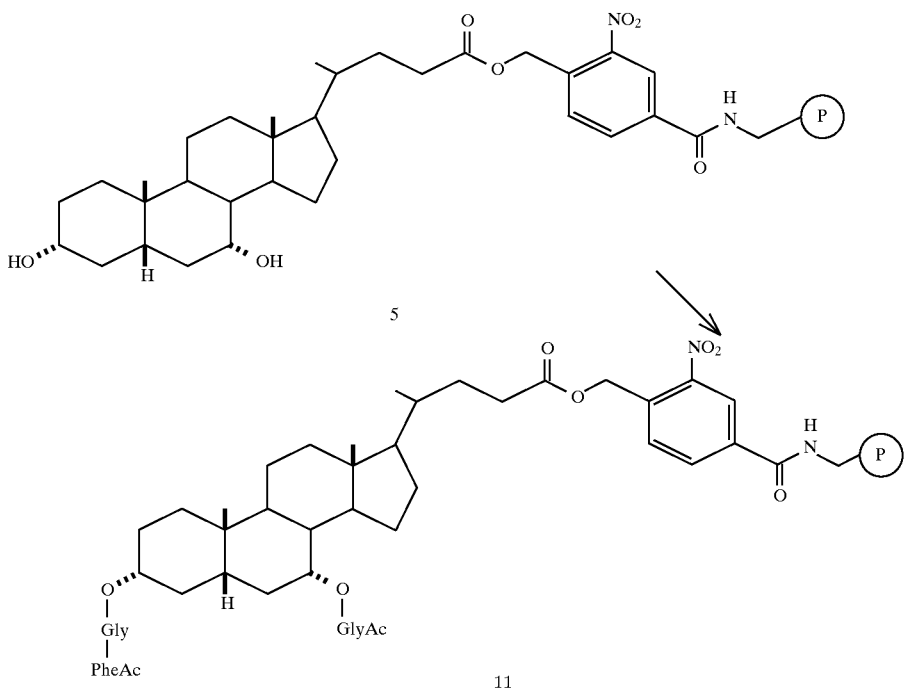

To the detachable beads 5 (200 mg, 0.09 mmol) was added diisopropylethyl amine (110 μL, 0.6 mmol) in 1 mL N,N-dimethylformamide followed by the addition of 9-fluorenylmethyloxycarbonyl-GlyF (135 mg, 0.45 mmol) in 1 mL N,N-dimethylformamide. After shaking at room temperature for 3 hours, reagents were filtered and the beads were washed with N,N-dimethylformamide (5 mL) once. The resulting beads were retreated with diisopropylethyl amine and 9-fluroenylmethyloxycarbonyl-GlyF in N,N-dimethyformamide twice under the same conditions and then washed with 3×N,N-dimethylformamide to give $C_3$-OGly-9-fluorenylmethyloxycarbonyl, $C_7$—OH beads.

To the above beads were added diisopropylethyl amine (110 μL, 0.6 mmol) and 4-Dimethylaminopyridine (11 mg, 0.09 mmol) in 1 mL N,N-dimethylformamide followed by the addition of 9-Fluorenylmethyloxycarbonyl-GlyF (135 mg, 0.45 mmol) in 1 mL N,N-dimethylformamide. After shaking at room temperature for 1 h, reagents were filtered and the beads were washed with N,N-dimethylformamide (5 mL) once. The resulting beads were retreated with diisopropylethyl amine, 4-Dimethylaminopyridine and 9-Fluorenylmethyloxycarbonyl-GlyF in N,N-dimethylformamide twice under the same conditions and then washed with 3×N,N-dimethylformamide (5 mL, 2 min each), 3×i-PrOH (5 mL, 2 min each) and 5 CH$_2$Cl$_2$ (5 mL, 2 min each), and then dried on pump to afford beads 11.

C$_7$—OH beads (4.2 g, slightly yellow beads).

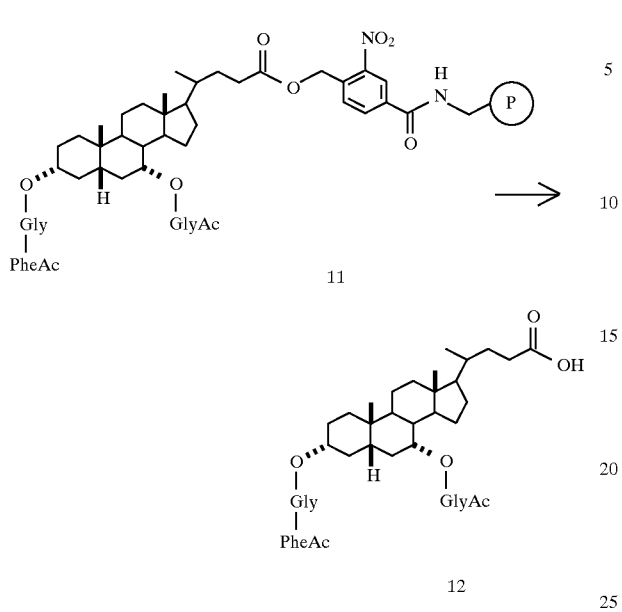

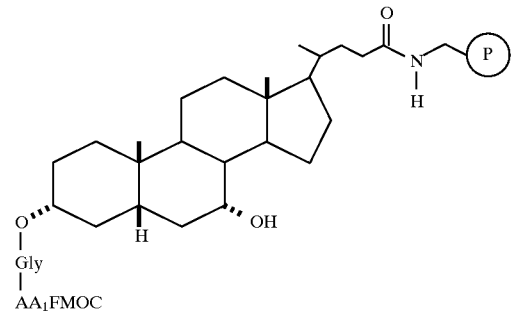

The above beads 11 (40~50 mg) and 500 μL N,N-dimethyformamide in a capped 1 mL test tube were under Ultraviolet light for 12 hours. The beads were filtered, and the filtrate was concentrated to give 12 as a waxy solid. The NMR spectrum of 12 indicates that the acylation of C$_7$—OH is complete.

The Synthesis of a Gly-library

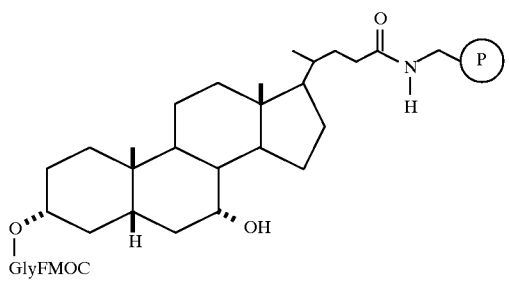

To a 50 mL reaction vessel containing 3 g aminomethyl resin (1.8 mmol, 0.6 mmol/g) were added 1-hydroxybenzotriazole (675 mg, 5.0 mmol), DIC (660 μL, 4.5 mmol) and chenodeoxycholic acid (1.8 g, 4.5 mmol) in 30 mL N,N-dimethylformamide. The reaction mixtures were shaken at room temperature for 6–8 hours. When the Kaiser test indicated the completion of the coupling reaction, the beads in the reaction vessel were washed twice with N,N-dimethylformamide (30 mL each), three times with CH$_2$Cl$_2$ (30 mL each) and dried.

To the above chenodeoxycholic acid beads was added diisopropylethyl amine (2.1 mL, 12 mmol) in N,N-dimethylformamide (20 mL) followed by the addition of 9-Fluorenylmethyloxycarbonyl-GlyF (2.7 g, 9 mmol) in 10 mL N,N-dimethylformamide. After shaking at room temperature for 3 hours, solvents and reagents were filtered and the beads were washed with N,N-dimethylformamide once. The resulting beads were retreated with diisopropylethyl amine and 9-Fluorenylmethyloxycarbonyl twice under the same conditions, and then washed with 3×N,N-dimethyformamide, 2×i-PrOH, 5×CH$_2$Cl$_2$, and dried on pump to give the C$_3$-OGly9-Fluorenylmethyloxycarbonyl, Ten equal portions (400 mg~0.18 mmol) of the above resin were placed into ten reaction vessels which were labeled as 1,2,3, . . . ,10. Each portion of the beads was treated with 1:1 N,N-dimethylformamide/piperidine (10 mL) at room temperature for 30 min to remove 9-Fluorenylmethyloxycarbonyl protecting group. After washing the beads with 4×N,N-dimethylformamide, the tag molecules (1.8×10$^{-3}$ mmol), 1-hydroxybenzotrazole (13 mg, 0.09 mmol, 50 eq.) and DIC (14 μL, 0.09 mmol, 50 eq.) in 4 mL N,N-dimethylformamide were added to each reaction vessel as the following manner:

| Tag molecules | Amount of Tags | Reaction vessel |
|---|---|---|
| T$_1$, C$_3$, 2, 4, 5 Cl$_3$ | 0.9 mg | 1 |
| T$_2$, C$_3$, 2, 4, 6 Cl$_3$ | 0.9 mg | 2 |
| T$_3$, C$_4$, 2, 4, 5 Cl$_3$ | 0.9 mg | 3 |
| T$_4$, C$_5$, 2, 4, 6 Cl$_3$ | 0.9 mg | 4 |
| T$_1$, T$_2$ | T$_1$, 0.9 mg; T$_2$, 0.9 mg | 5 |
| T$_1$, T$_3$ | T$_1$, 0.9 mg; T$_3$, 0.9 mg | 6 |
| T$_1$, T$_4$ | T$_1$, 0.9 mg; T$_4$, 0.9 mg | 7 |
| T$_2$, T$_3$ | T$_1$, 0.9 mg; T$_3$, 0.9 mg | 8 |
| T$_2$, T$_4$ | T$_1$, 0.9 mg; T$_4$, 0.9 mg | 9 |
| T$_3$, T$_4$ | T$_1$, 0.9 mg; T$_4$, 0.9 mg | 10 |

After shaking 12 hours in the dark at room temperature, the beads in each reaction vessel were washed with 4×CH$_2$Cl$_2$ (10 mL each). 9-Fluorenylmethyloxycarbonyl-Amino acid (0.5 mmol), 1-hydroxybenzotriazole (70 mg, 0.5 mmol) and DIC (80 μL, 0.5 mmol) in 4 mL N,N-dimethylformamide were added to each reaction vessels as:

| Amino Acids | Amount of Amino Acids | Reaction Vessel |
|---|---|---|
| Ala | 156 mg | 1 |
| Val | 170 mg | 2 |
| Leu | 177 mg | 3 |
| Phe | 194 mg | 4 |
| Pro | 170 mg | 5 |
| Ser | 192 mg | 6 |
| Thr | 199 mg | 7 |
| Lys | 235 mg | 8 |
| Glu | 213 mg | 9 |
| Asp | 206 mg | 10 |

When the resin in each reaction vessel gave a negative Kaiser test, normally 3 h at room temperature. Then the beads in ten reaction vessels were combined in a 50 mL reaction vessel and washed with 2×N,N-dimethylformamide (30 mL, 2 min each), 3×i-PrOH (30 mL, 2 min each) and 5×CH$_2$Cl$_2$ (30 mL, 2 min each), and dried to afford C$_3$OGlyAA$_1$-9-Fluorenylmethyloxycarbonyl,C$_7$—OH beads.

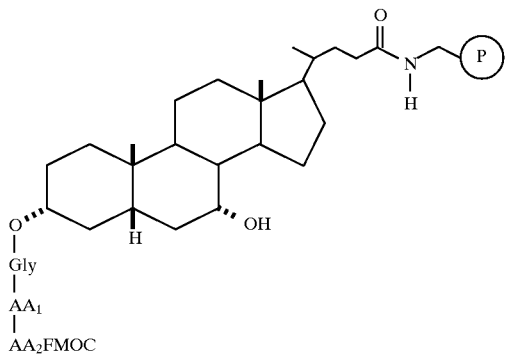

Gly
|
AA₁
|
AA₂FMOC

The second step AA₂ was initiated by the division of the above C₃-OGlyAA₁FMOC, C₇—OH beads into ten equal portions. The labelling and coupling conditions were exactly same as the first AA₁. The tag molecules used to encode the second step synthesis are listed below:

| Tag molecules | Amount of Tags | Reaction vessel |
| --- | --- | --- |
| T₅, C₆, 2, 4, 5 Cl₃ | 1.0 mg | 1 |
| T₆, C₆, 2, 4, 6 Cl₃ | 1.0 mg | 2 |
| T₇, C₇ 2, 4, 5 Cl₃ | 1.0 mg | 3 |
| T₈, C₇, 2, 4, 6 Cl₃ | 1.0 mg | 4 |
| T₅, T₆ | T₅, 1.0 mg; T₆, 1.0 mg | 5 |
| T₅, T₇ | T₅, 1.0 mg; T₇, 1.0 mg | 6 |
| T₅, T₈ | T₅, 1.0 mg; T₈, 1.0 mg | 7 |
| T₆, T₇ | T₆, 1.0 mg; T₇, 1.0 mg | 8 |
| T₆, T₈ | T₆, 1.0 mg; T₈, 1.0 mg | 9 |
| T₇, T₈ | T₇, 1.0 mg; T₈, 1.0 mg | 10 |

After labelling, coupling and washing cycle, the C₃OGlyAA₁AA₂FMOC, C₇—OH beads were obtained.

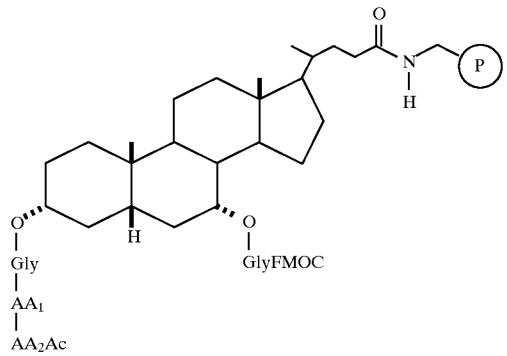

Gly
|
AA₁
|
AA₂Ac

GlyFMOC

The above C₃-OGlyAA₁AA₂FMOC, C₇—OH beads were treated with 1:1 DMF/Piperidine (30 mL) to remove the FMOC-group. After under shaking at room temperature for 30 min, the beads were washed with 4×DMF and treated with HOAc (530 μL, 9 mmol), HOBT (1.35 g, 10 mmol) and DIC (1.4 mL, 9 mmol) in 35 mL DMF. The reaction mixtures were shaken for 2 h until the Kaiser test indicated the completion of the reaction. The beads were then thoroughly washed with 2×DMF (30 mL, 2 min each), 3×i-PrOH (30 mL, 2 min each) and 5×CH₂Cl₂ (30 mL, 2 min each), and then dried to give the C₃-OGlyAA₁AA₂Ac, C₇—OH beads.

To the above beads were added DIPEA (2.1 mL, 12 mmol) and DMAP (220 mg, 1.8 mmol) in 20 mL DMF followed by the addition of FMOC-GlyF (2.7 g, 9 mmol) in 15 mL DMF. After shaking at room temperature for 1 h, reagents were filtered and the beads were washed with DMF (30 mL) once. The resulting beads were retreated with DIPEA, DMAP and FMOC-GlyF in DMF twice under the same conditions and then washed with 3×DMF, 3×i-PrOH and 5×CH₂Cl₂, and then dried to give C₃-OGlyAA₁AA₂Ac, C₇-OGlyFMOC beads.

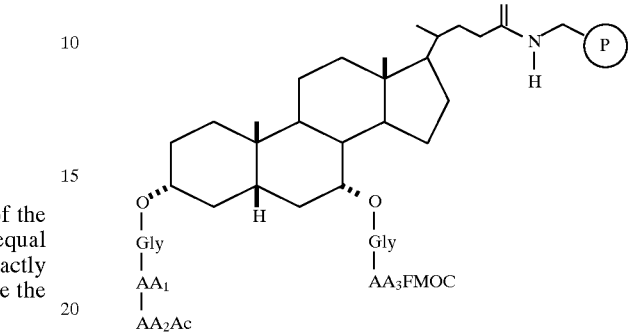

Gly
|
AA₁
|
AA₂Ac

Gly
|
AA₃FMOC

The third step AA₃ was also initiated by the division of the above C₃-OGlyAA₁AA₂Ac, C₇-OGlyFMOC beads into ten equal portions. The labelling and coupling conditions were exactly the same as the first steps. The tag molecule used to encode the third step synthesis are listed below:

| Tag Molecules | Amount of Tags | Reaction vessel |
| --- | --- | --- |
| T₉, C₈, 2, 4, 5 Cl₃ | 1.0 mg | 1 |
| T₁₀, C₈, 2, 4, 6 Cl₃ | 1.0 mg | 2 |
| T₁₁, C₉, 2, 4, 5 Cl₃ | 1.1 mg | 3 |
| T₁₂, C₉, 2, 4, 6 Cl₃ | 1.1 mg | 4 |
| T₉, T₁₀ | T₉, 1.0 mg; T₁₀, 1.0 mg | 5 |
| T₉, T₁₁ | T₉, 1.0 mg; T₁₁, 1.1 mg | 6 |
| T₉, T₁₂ | T₉, 1.0 mg; T₁₂, 1.1 mg | 7 |
| T₁₀, T₁₁ | T₁₀, 1.0 mg; T₁₁, 1.1 mg | 8 |
| T₁₀, T₁₂ | T₁₀, 1.0 mg; T₁₂, 1.1 mg | 9 |
| T₁₁, T₁₂ | T₁₁, 1.1 mg; T₁₂, 1.1 mg | 10 |

After labelling, coupling and washing cycle, the C₃-OGlyAA₁AA₂Ac, C₇-OGlyAA₃FMOC beads were obtained.

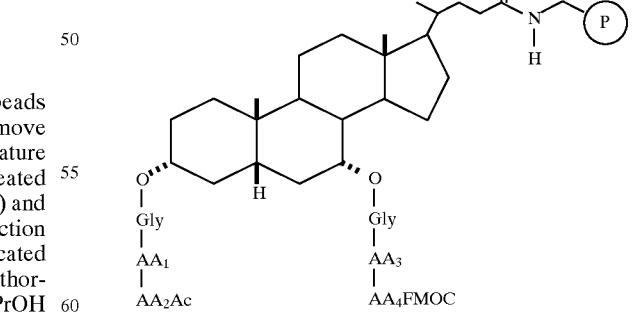

Gly
|
AA₁
|
AA₂Ac

Gly
|
AA₃
|
AA₄FMOC

The labelling and coupling conditions of the fourth step AA₄ were exactly the same as that of the previous steps. At the end of the synthesis, the C₃-OGlyAA₁AA₂Ac, C₇OGlyAA₃AA₄FMOC were obtained. The tag molecules used for this step are listed below:

| Tag molecules | Amount of Tags | Reaction vessels |
|---|---|---|
| $T_{13}$, $C_{10}$, 2, 4, 5 $Cl_3$ | 1.1 mg | 1 |
| $T_{14}$, $C_{10}$, 2, 4, 6 $Cl_3$ | 1.1 mg | 2 |
| $T_{15}$, $C_{11}$, 2, 4, 5 $Cl_3$ | 1.1 mg | 3 |
| $T_{16}$, $C_{11}$, 2, 4, 6 $Cl_3$ | 1.1 mg | 4 |
| $T_{13}$, $T_{14}$ | $T_{13}$, 1.1 mg; $T_{14}$, 1.1 mg | 5 |
| $T_{13}$, $T_{15}$ | $T_{13}$, 1.1 mg; $T_{15}$, 1.1 mg | 6 |
| $T_{13}$, $T_{16}$ | $T_{13}$, 1.1 mg; $T_{16}$, 1.1 mg | 7 |
| $T_{14}$, $T_{15}$ | $T_{14}$, 1.1 mg; $T_{15}$, 1.1 mg | 8 |
| $T_{14}$, $T_{16}$ | $T_{14}$, 1.1 mg; $T_{16}$, 1.1 mg | 9 |
| $T_{15}$, $T_{16}$ | $T_{15}$, 1.1 mg; $T_{16}$, 1.1 mg | 10 |

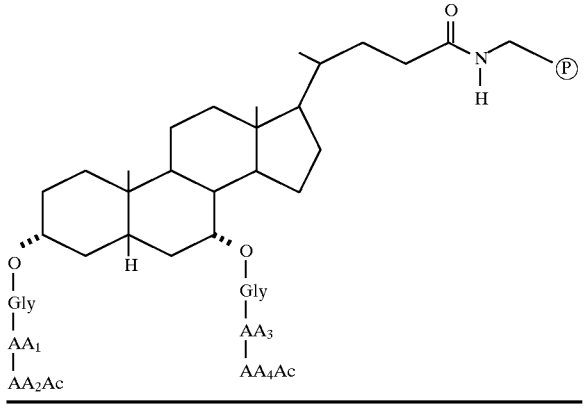

To the above $C_3$-OGlyAA$_1$AA$_2$Ac, $C_7$-OGlyAA$_3$AA$_4$FMOC beads was added 1:1 DMF/Piperidine (30 mL) to remove the FMOC-group. The reaction mixtures were shaken at room temperature for 30 min. and then the beads were washed with 4×DMF and treated with HOAC (530 μL, 9 mmol), HOBT (1.35 g, 10 mmol) and DIC (1,4 mL, 9 mmol) in 35 mL DMF. The reaction mixtures were shaken for 2 h until the Kaiser test indicated the completion of the reaction. The beads were then thoroughly washed with 2×DMF (30 mL, 2 min each), 3×i-PrOH (30 mL, 2 min each) and 5×CH$_2$Cl$_2$ (30 mL, 2 min each), and then dried to give the protected Gly-library.

The Deprotected Gly-Library

To the resulting $C_3$-OGly AA$_1$AA$_2$Ac, $C_7$-OGlyAA$_3$AA$_4$Ac beads (1.0 g) was added 25% TFA/CH$_2$Cl$_2$ solution (20 ml). The reaction vessel was shaken at room temperature for 1 h, and the beads were washed with 4×CH$_2$Cl$_2$, 3×i-PrOH and 5×CH$_2$Cl$_2$, and dried to afford the deprotected Glylibrary.

The synthesis of Pro-Library

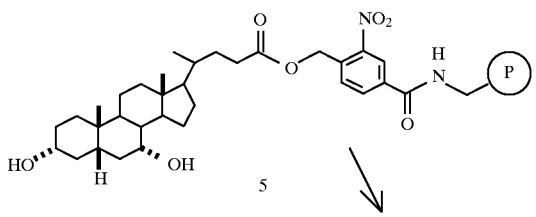

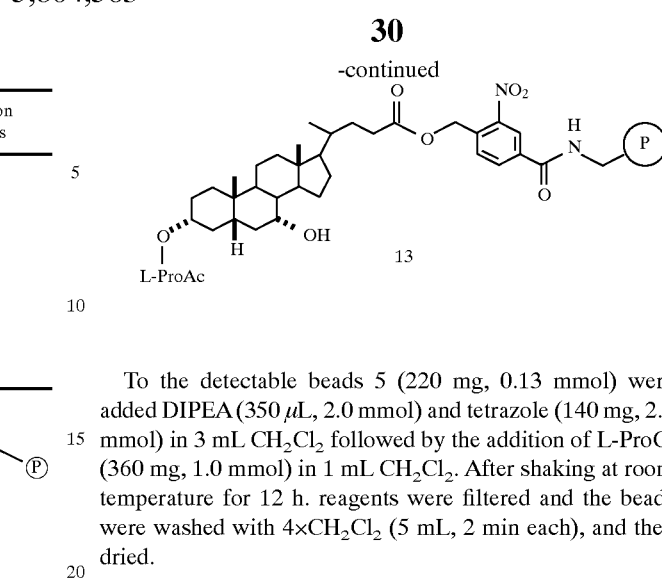

To the detectable beads 5 (220 mg, 0.13 mmol) were added DIPEA (350 μL, 2.0 mmol) and tetrazole (140 mg, 2.0 mmol) in 3 mL CH$_2$Cl$_2$ followed by the addition of L-ProCl (360 mg, 1.0 mmol) in 1 mL CH$_2$Cl$_2$. After shaking at room temperature for 12 h. reagents were filtered and the beads were washed with 4×CH$_2$Cl$_2$ (5 mL, 2 min each), and then dried.

To the above beads was added 1:1 DMF/piperidine (5 mL). The reaction vessel was shaken at room temperature for 30 min. and then the beads were washed with 4×DMF and treated with HOAc (39 μL, 0.65 mmol), HOBT (88 mg, 0.65 mmol) and DIC (100 μl, 0.65 mmol) in 4 mL DMF. The reaction mixtures were shaken for 2 h until the Kaiser test indicated the completion of the reaction. The beads were then thoroughly washed with 2×DMF (5 mL, 2 min each), 3×i-PrOH (5 mL, 2 min each) and 5×CH$_2$Cl$_2$ (5 mL, 2 min each), and then dried on pump to afford beads 13.

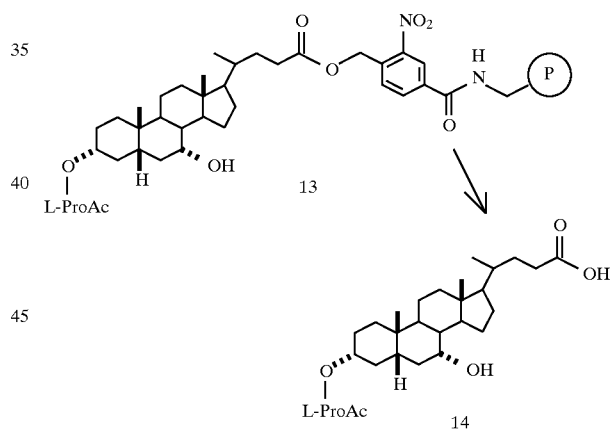

The beads 13 (25 mg) and 500 μL CH$_3$OH in a capped 1 mL test tube were under UV light for 12 h. The beads were filtered and the filtrate was concentrated to give 14 as a white solid. The NMR spectrum of 14 indicates that the selectivity for esterification of $C_3$—OH and $C_7$—OH is 25:1.

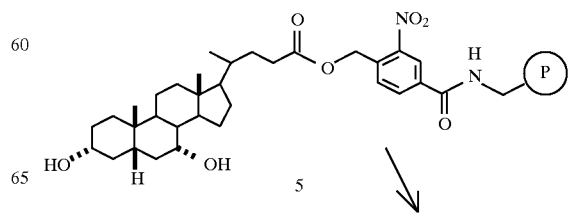

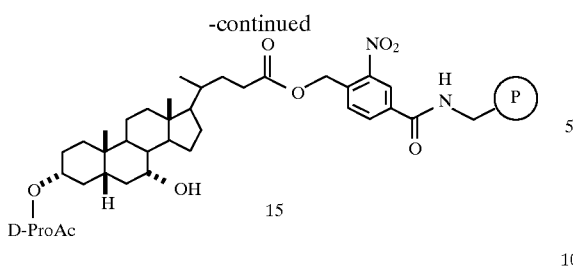

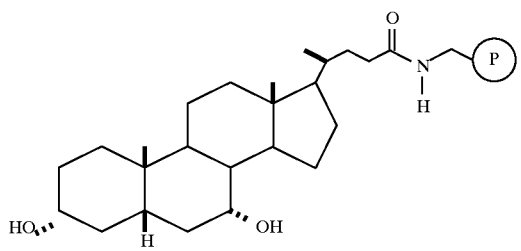

To the detectable beads 5 (220 mg, 0.13 mmol) were added DIPEA (350 μL, 2.0 mmol) and tetrazole (140 mg, 2.0 mmol) in 3 mL $Ch_2Cl_2$ followed by the addition of D-ProCl (360 mg, 1.0 mmol) in 1 mL $CH_2Cl_2$. After shaking at room temperature for 6 h, reagents were filtered and the beads were washed with 4×$CH_2Cl_2$ (5 mL, 2 min each), 2×$CH_3OH$ (5 mL, 2 min each) and 4×$CH_2Cl_2$ (5 mL, 2 min each), and then dried.

To the above beads was added 1:1 DMF/piperidine (5 mL). The reaction vessel was shaken at room temperature for 30 min. and then the beads were washed with 4×DMF and treated with HOAc (39 μL, 0.65 mmol), HOBT (88 mg, 0.65 mmol) and DIC (100 μl, 0.65 mmol) in 4 mL DMF. The reaction mixtures were shaken for 2 h until the Kaiser test indicated the completion of the reaction. The beads were then thoroughly washed with 2×DMF (5 mL, 2 min each), 3×i-PrOH (5 mL, 2 min each) and 5×$CH_2Cl_2$ (5 mL, 2 min each), and then dried on pump to afford beads 15.

To a 50 mL reaction vessel containing 2 g aminomethyl resin (1.8 mmol, 0.9 mmol/g) were added HOBT (675 mg, 5.0 mmol), DIC (660 μL, 4.5 mmol) and chenodeoxycholic acid (1.8 g, 4.5 mmol) in 30 mL DMF. The reaction mixtures were shaken at room temperature for 6.8 h. When the Kaiser test indicated the completion of the coupling reaction, the beads in the reaction vessel were washed with 2×DMF (30 mL, 2 min each), 3×i-PrOH (30 mL, 2 min each), 5×$CH_2Cl_2$ (30 mL, 2 min each) and dried to give the chenodeoxycholic acid beads (2.7 g).

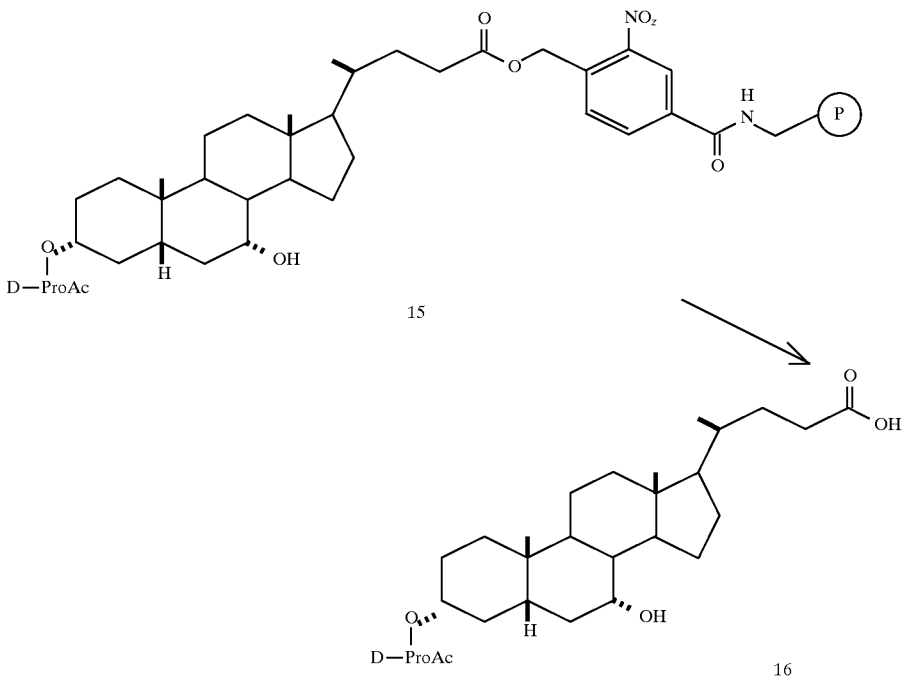

The beads 15 (25 mg) and 500 μL $CH_3OH$ in a capped 1 mL test tube were under UV light for 12 h. The beads were filtered, and the filtrate was concentrated to give 16 as a white solid. The NMR spectrum of 16 indicates that the selectivity for esterification of $C_3$—OH and $C_7$—OH is 20:1.

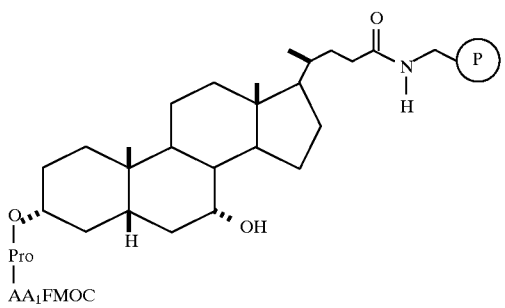

Two equal portions (1.3 g, 0.9 mmol) of the above resin were placed into two reaction vessels which were labeled as A and B.

Beads in the reaction vessel A were treated with DIPEA (2.4 mL, 14 mmol) and tetrazole (980 mg, 14 mmol) in 20 mL $CH_2Cl_2$ followed by the addition of L-ProCl (2.4 g, 7 mmol) in 10 mL $CH_2Cl_2$. After under shaking at room temperature for 12 h, the beads were thoroughly washed with 3×$CH_2Cl_2$, 2×i-PrOH and 4×$CH_2Cl_2$ and dried. The resulting beads were divided into ten equal portions (150 mg, ~0.09 mmol) and placed into ten reaction vessels. The reaction vessels were labeled as 1,2, . . . , 10. Each portion of the beads was treated with 1:1 DMF/piperidine (10 mL) at room temperature for 30 min to remove FMOC-protecting group. After washing the beads with 4×DMF, the tag molecules (0.9×$10^{-3}$ mmol), HOBT (9.5 mg, 0.07 mmol, 75 eq.) and DIC (11 μL, 0.07 mmol, 75 eq.) in 4 mL DMF were added to each reaction vessel in the following manner:

| Tag molecules | Amount of Tags | Reaction vessel |
|---|---|---|
| $T_1$, $T_3$ | $T_1$, 0.7 mg; $T_3$, 0.6 mg | 1 |
| $T_1$, $T_4$ | $T_1$, 0.7 mg; $T_4$, 0.6 mg | 2 |
| $T_1$, $T_5$ | $T_1$, 0.7 mg; $T_5$, 0.6 mg | 3 |
| $T_1$, $T_6$ | $T_1$, 0.7 mg; $T_6$, 0.6 mg | 4 |
| $T_1$, $T_3$, $T_4$ | $T_1$, 0.7 mg; $T_3$, 0.6 mg; $T_4$, 0.6 mg | 5 |
| $T_1$, $T_3$, $T_5$ | $T_1$, 0.7 mg; $T_3$, 0.6 mg; $T_5$, 0.6 mg | 6 |
| $T_1$, $T_3$, $T_6$ | $T_1$, 0.7 mg; $T_4$, 0.6 mg; $T_6$, 0.6 mg | 7 |
| $T_1$, $T_3$, $T_5$ | $T_1$, 0.7 mg; $T_4$, 0.6 mg; $T_5$, 0.6 mg | 8 |
| $T_1$, $T_3$, $T_6$ | $T_1$, 0.7 mg; $T_4$, 0.6 mg; $T_6$, 0.6 mg | 9 |
| $T_1$, $T_5$, $T_6$ | $T_1$, 0.7 mg; $T_5$, 0.6 mg; $T_6$, 0.6 mg | 10 |

After shaking for 12 h in the dark at room temperature, the beads in each reaction vessel were washed with 4×$CH_2Cl_2$ (10 mL each) FMOC-AA (0.25 mmol), OBT 35 mg, 0.25 mmol, and DIC (40 μL, 0.25 mmol) in 4 mL DMF were added to each reaction vessels as follows:

| Amino Acids | Amount of Amino Acids | Reaction Vessel |
|---|---|---|
| Ala | 78 mg | 1 |
| Val | 85 mg | 2 |
| Leu | 89 mg | 3 |
| Phe | 97 mg | 4 |
| Pro | 85 mg | 5 |
| Ser | 96 mg | 6 |
| Thr | 100 mg | 7 |
| Lys | 120 mg | 8 |
| Glu | 105 mg | 9 |
| Asp | 103 mg | 10 |

When the resin in each reaction vessel gave a negative Kaiser test, normally 3 h at room temperature. Then the beads in ten reaction vessels were combined in a 50 mL reaction vessel and washed with 2×DMF (30 mL, 2 in each), 3×i-PrOH (30 mL, 2 min each) and 5×$CH_2Cl_2$ (30 mL, 2 min each), and dried to afford $C_3$—O—L-ProAA$_1$FMOC, $C_7$—OH beads.

Beads in the reaction vessel B were treated with DIPEA (2.4 mL, 14 mmol) and tetrazole (980 mg, 14 mmol) in 20 mL $CH_2Cl_2$. After shaking at room temperature for 6 h, the beads were thoroughly washed with 3×$CH_2Cl_2$, 2×i-PrOH and 4×$CH_2Cl_2$ and dried. The resulting beads were divided into ten equal portions (150 mg, ~0.09 mmol) and placed into ten reaction vessels. The reaction vessels wee labeled as 1,2, . . . , 10. Each portion of the beads was treated with 1:1 DMF/piperidine (10 mL) at room temperature for 30 min to remove FMOC-protecting group. After washing the beads with 4×DMF, the tag molecules 10.9×$10^{-3}$ mmol), HOBT (9.5 mg, 0.07 mmol, 75 eq.) and DIC (11 μL, 0.07 mmol, 75 eq.) in 4 mL DMF were added to each reaction vessel in the following manner:

| Tag molecules | Amount of Tags | Reaction vessel |
|---|---|---|
| $T_2$, $T_3$ | $T_2$, 0.7 mg; $T_3$, 0.6 mg | 1 |
| $T_2$, $T_4$ | $T_2$, 0.7 mg; $T_4$, 0.6 mg | 2 |
| $T_2$, $T_5$ | $T_2$, 0.7 mg; $T_5$, 0.6 mg | 3 |
| $T_2$, $T_6$ | $T_2$, 0.7 mg; $T_6$, 0.6 mg | 4 |
| $T_2$, $T_3$, $T_4$ | $T_2$, 0.7 mg; $T_3$, 0.6 mg; $T_4$, 0.6 mg | 5 |
| $T_2$, $T_3$, $T_5$ | $T_2$, 0.7 mg; $T_3$, 0.6 mg; $T_5$, 0.6 mg | 6 |
| $T_2$, $T_3$, $T_6$ | $T_2$, 0.7 mg; $T_3$, 0.6 mg; $T_6$, 0.6 mg | 7 |
| $T_2$, $T_4$, $T_5$ | $T_2$, 0.7 mg; $T_4$, 0.6 mg; $T_5$, 0.6 mg | 8 |
| $T_2$, $T_4$, $T_6$ | $T_2$, 0.7 mg; $T_4$, 0.6 mg; $T_6$, 0.6 mg | 9 |
| $T_2$, $T_5$, $T_6$ | $T_2$, 0.7 mg; $T_5$, 0.6 mg; $T_6$, 0.6 mg | 10 |

After shaking 12 h in the dark at room temperature, the beads in each reaction vessel were washed with 4×$CH_2Cl_2$ (10 mL each). FMOC-AA (0.25 mmol), HOBT (35 mg, 0.25 mmol) and DIC (40 μL, 0.25 mmol) in 4 mL DMF were added to each reaction vessels as:

| Amino Acids | Amount of Amino Acids | Reaction Vessel |
|---|---|---|
| Alan | 78 mg | 1 |
| Val | 85 mg | 2 |
| Leu | 89 mg | 3 |
| Phe | 97 mg | 4 |
| Pro | 85 mg | 5 |
| Ser | 96 mg | 6 |
| Thr | 100 mg | 7 |
| Lys | 120 mg | 8 |
| Glu | 105 mg | 9 |
| Asp | 103 mg | 10 |

When the resin in each vessel gave a negative Kaiser test, normally 3 hours at room temperature. Then the beads in ten reaction vessels were combined in a 50 mL reaction vessel and washed with 2×DMF (30 mL, 2 min each), 3×i-PrOH (30 mL, 2 min each) and 5×$CH_2Cl_2$ (30 mL, 2 min each), and dried to afford $C_3$—O—D-ProAA$_1$FMOC, $C_7$—OH beads.

The above D and L Pro beads were then combined in a single reaction vessel. The combined beads suspended in 30 mL $CH_2Cl_2$ were shaken at room temperature for 30 min. The solvent was filtered and the beads were dried to give $C_3$—O—DL-ProAA$_1$FMOC, $C_7$—OH beads.

The tag molecules used for this step synthesis are:

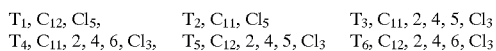

T₁, C₁₂, Cl₅,        T₂, C₁₁, Cl₅        T₃, C₁₁, 2, 4, 5, Cl₃
T₄, C₁₁, 2, 4, 6, Cl₃,    T₅, C₁₂, 2, 4, 5, Cl₃    T₆, C₁₂, 2, 4, 6, Cl₃

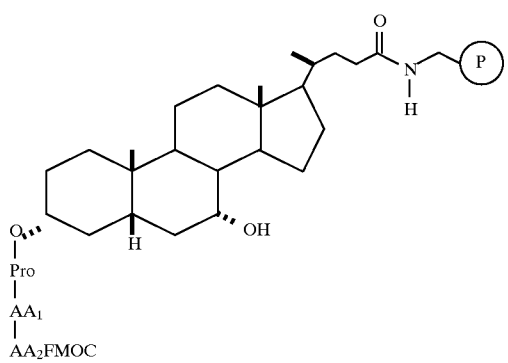

The second step AA₂ was initiated by the division of the above C₃—O—DL-ProAA₁FMOC, C₇—OH beads into ten equal portions. Each portion of the beads was treated with 1:1 DMF/piperidine (10 mL) at room temperature for 30 min to remove FMOC protecting group. After washing the beads with 4×DMF, the tag molecules (1.8×10⁻³ mmol), HOBT (13 mg, 0.09 mmol, 50 E1.) and DIC (14 μL, 0.09 mmol, 50 eq.) in 4 mL DMF were added to each reaction vessel in the following manner:

| Tag Molecules | Amount of Tags | Reaction vessel |
|---|---|---|
| T₇, C₉, 2,4,5 Cl₃ | 1.0 mg | 1 |
| T₈, C₉, 2,4,6 Cl₃ | 1.0 mg | 2 |
| T₉, C₁₀, 2,4,5 Cl₃ | 1.0 mg | 3 |
| T₁₀, C₁₀, 2,4,6 Cl₃ | 1.0 mg | 4 |
| T₇, T₈ | T₇, 0.9 mg; T₈, 0.9 mg | 5 |
| T₇, T₉ | T₇, 0.9 mg; T₉, 0.9 mg | 6 |
| T₇, T₁₀ | T₇, 0.9 mg; T₁₀, 0.9 mg | 7 |
| T₈, T₉ | T₈, 0.9 mg; T₉, 0.9 mg | 8 |
| T₈, T₁₀ | T₈, 0.9 mg; T₁₀, 0.9 mg | 9 |
| T₉, T₁₀ | T₉, 0.9 mg; T₁₀, 0.9 mg | 10 |

After shaking 12 h in the dark at room temperature, the beads in each reaction vessel were washed with 4×CH₂Cl₂ (10 mL each). FMOC-AA (0.5 mmol), HOBT (70 mg, 0.5 mmol) and DIC (80 μL, 0.5 mmol) in 4 mL DMF were added to each reaction vessels as:

| Amino Acids | Amount of Amino Acids | Reaction vessel |
|---|---|---|
| Ala | 156 mg | 1 |
| Val | 170 mg | 2 |
| Leu | 177 mg | 3 |
| Phe | 194 mg | 4 |
| Pro | 170 mg | 5 |
| Ser | 192 mg | 6 |
| Thr | 199 mg | 7 |
| Lys | 235 mg | 8 |
| Glu | 213 mg | 9 |
| Asp | 206 mg | 10 |

When the resin in each reaction vessel gave a negative Kaiser test, normally 3 h at room temperature. Then the beads in ten reaction vessels were combined in a 50 mL reaction vessel and washed with 2×DMF (30 mL, 2 min each), 3×i-PrOH (30 mL, 2 min each) and 5×CH₂Cl₂ (30 mL, 2 min each), and dried to afford C₃-OProAA₁AA₂FMOC, C₇—OH beads.

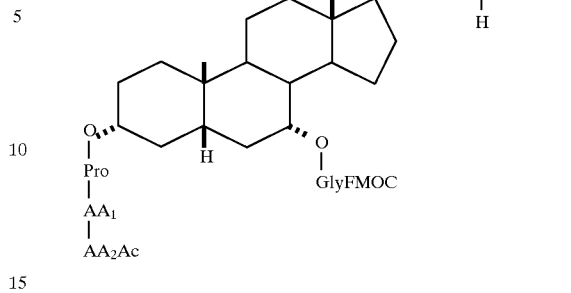

The above C₃-OProAA₁AA₂FMOC, C₇—OH beads were treated with 1:1 DMF/Piperidine (30 mL) to remove the FMOC-group. After under shaking at room temperature for 30 min. the beads were washed with 4×DMF and treated with HOAc (530 μL, 9 mmol), HOBT (1.35 g, 10 mmol) and DIC 1.4 mL, 9 mmol) in 35 mL DMF. The reaction mixtures were shaken for 2 h until the Kaiser test indicated the completion of the reaction. The beads were then thoroughly washed with 2×DMF (30 mL, 2 min each), 3×i-PrOH (30 mL, 2 min each) and 5×CH₂Cl₂(30 mL, 2 min each), and then dried to give the C₃-OProAA₁AA₂Ac, C₇—OH beads.

To the above beads were added DIPEA (2.1 mL, 12 mmol) and DMAP (220 mg, 1.8 mmol) in 20 mL DMF followed by the addition of FMOC-GlyF (2.7 g, 9 mmol) in 15 mL DMF. After shaking at room temperature for 1 h, reagents were filtered and the beads were washed with DMF (30 mL) once.

The resulting beads were retreated with DIPEA, DMAP and FMOC-GlyF in DMF twice under the same conditions and then washed with 3×DMF, 3×i-PrOH and 5×CH₂Cl₂, and then dried to give C₃-OProAA₁AA₂Ac, C₇-OGlyFMOC beads.

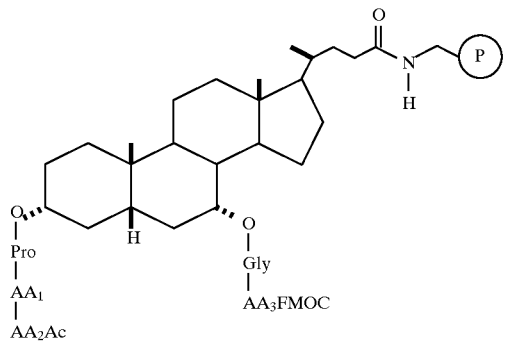

The third step AA₃ was also initiated by the division of the above C₃-OProAA₁AA₂Ac, C₇-OGlyFMOC beads into ten equal portions. The labelling and coupling conditions were exactly the same as the second steps. The tag molecules used to encode the third step synthesis are listed below:

| Tag molecules | Amount of Tags | Reaction vessel |
|---|---|---|
| T₁₁, C₇, 2,4,5 Cl₃ | 1.0 mg | 1 |
| T₁₂, C₇, 2,4,6 Cl₃ | 1.0 mg | 2 |
| T₁₃, C₈, 2,4,5 Cl₃ | 1.0 mg | 3 |
| T₁₄, C₈, 2,4,6 Cl₃ | 1.0 mg | 4 |
| T₁₁, T₁₂ | T₁₁, 1.0 mg; T₁₂, 1.0 mg | 5 |
| T₁₁, T₁₃ | T₁₁, 1.0 mg; T₁₃, 1.0 mg | 6 |

-continued

| Tag molecules | Amount of Tags | Reaction vessel |
|---|---|---|
| $T_{11}, T_{14}$ | $T_{11}$, 1.0 mg; $T_{14}$, 1.0 mg | 7 |
| $T_{12}, T_{13}$ | $T_{12}$, 1.0 mg; $T_{13}$, 1.0 mg | 8 |
| $T_{12}, T_{14}$ | $T_{12}$, 1.0 mg; $T_{14}$, 1.0 mg | 9 |
| $T_{13}, T_{14}$ | $T_{13}$, 1.0 mg; $T_{14}$, 1.0 mg | 10 |

After labelling, coupling and washing cycles, the $C_3$-OProAA$_1$AA$_2$Ac, $C_7$-OGlyAA$_3$FMOC beads were obtained.

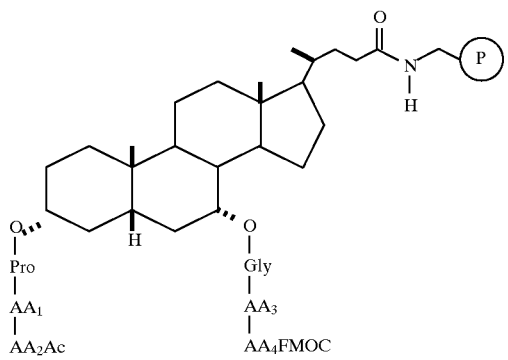

The labelling and coupling conditions of the fourth step AA$_4$ were exactly same as that of the second step. At the end of the synthesis, the $C_3$-OProAA$_1$AA$_2$Ac, $C_7$-OGlyAA$_3$FMOC beads were obtained.

The tag molecules used for this step are listed below:

| Tag molecules | Amount of Tags | Reaction vessel |
|---|---|---|
| $T_{15}$, $C_4$, 2, 4, 5 Cl$_3$ | 1.0 mg | 1 |
| $T_{16}$, $C_5$, 2, 4, 6 Cl$_3$ | 1.0 mg | 2 |
| $T_{17}$, $C_6$, 2, 4, 5 Cl$_3$ | 1.0 mg | 3 |
| $T_{18}$, $C_6$, 2, 4, 6 Cl$_3$ | 1.0 mg | 4 |
| $T_{15}, T_{16}$ | $T_{15}$, 0.9 mg; $T_{16}$, 0.9 mg | 5 |
| $T_{15}, T_{17}$ | $T_{15}$, 0.9 mg; $T_{17}$, 0.9 mg | 6 |
| $T_{15}, T_{18}$ | $T_{15}$, 0.9 mg; $T_{18}$, 0.9 mg | 7 |
| $T_{16}, T_{17}$ | $T_{16}$, 0.9 mg; $T_{17}$, 0.9 mg | 8 |
| $T_{16}, T_{18}$ | $T_{16}$, 0.9 mg; $T_{18}$, 0.9 mg | 9 |
| $T_{17}, T_{18}$ | $T_{16}$, 0.9 mg; $T_{18}$, 0.9 mg | 10 |

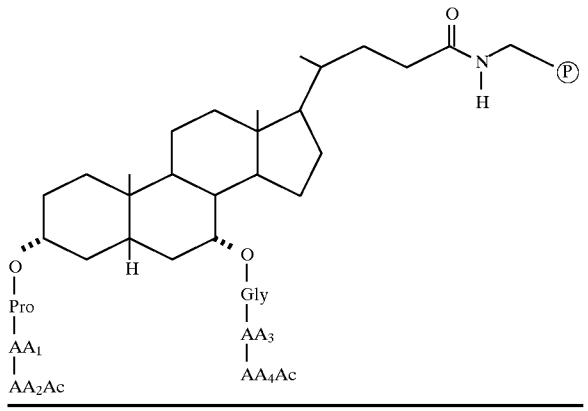

To the above $C_3$-OProAA$_1$AA$_2$Ac, $C_7$-OGlyAA$_3$FMOC beads was added 1:1 N, N-Dimethylformamide/Piperdine (30 mL) to remove the 9-Fluorenylmethloxycarbonyl-group. The reaction mixtures were shaken at room temperature for 30 min. and then the beads were washed with 4×N, N-Dimethylformamide and treated with Acetic Acid (530 µL, 9 mmol), 1-hydroxybenzotriazole (1.35 g, 10 mmol) and DIC (1.4 mL, 9 mmol) in 35 mL N, N-Dimethylformamide. The reaction mixtures were shaken for 2 hours until the Kaiser test indicated the completion of the reaction. The beads were then thoroughly washed with 2×DMF (30 mL, 2 min each), 3×i-PrOH (30 mL, 2 min each) and 5×CH$_2$Cl$_2$, 3×i-PrOH and 5×CH$_2$Cl$_2$, and dried to afford the deprotected Pro-Library.

Figure 4:
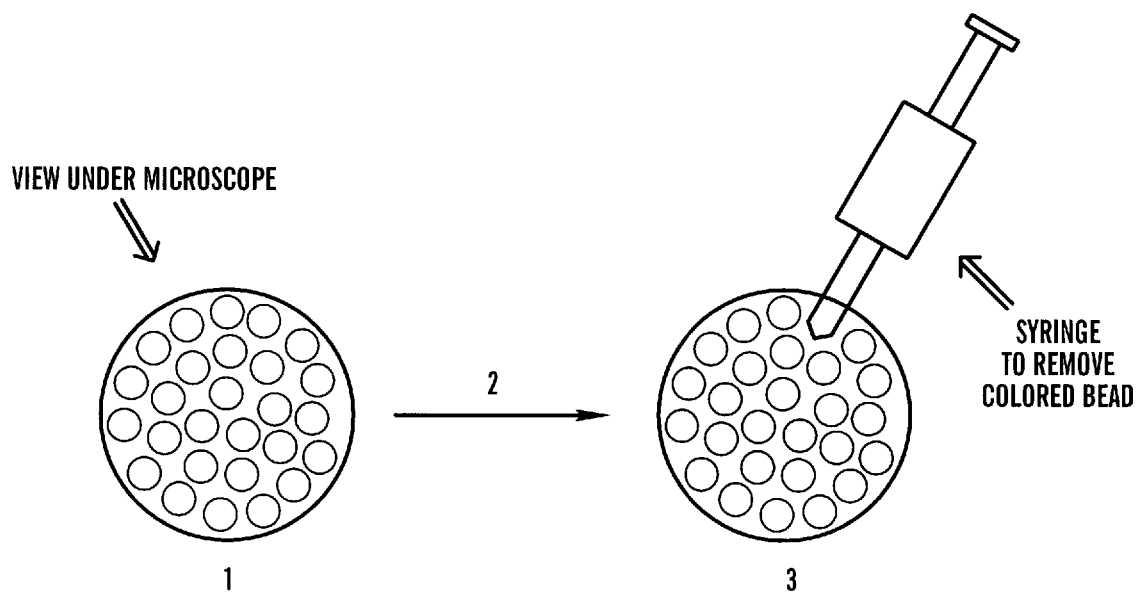
FIG. 4.

A color assay method was developed for screening receptor library beads. The color dye used is Disperse Red 1 (available from Aldrich Inc.), a neutral diazo dye whose λmax is at 502 nm. Red color in various organic solvents is visible at concentrations as low as 100 µM. The method is shown in FIG. 4 wherein 1 represents a supply of before treatment with a colored substrate; 2 represents the addition of a colored substrate; and 3 represents the resulting beads. In the assay, a solution of the colored substrate in an organic solvent is added to the supply of beads and the mixture is allowed to sit for one day, resulting in equilibration between the beads and the substrate.

Figure 5:
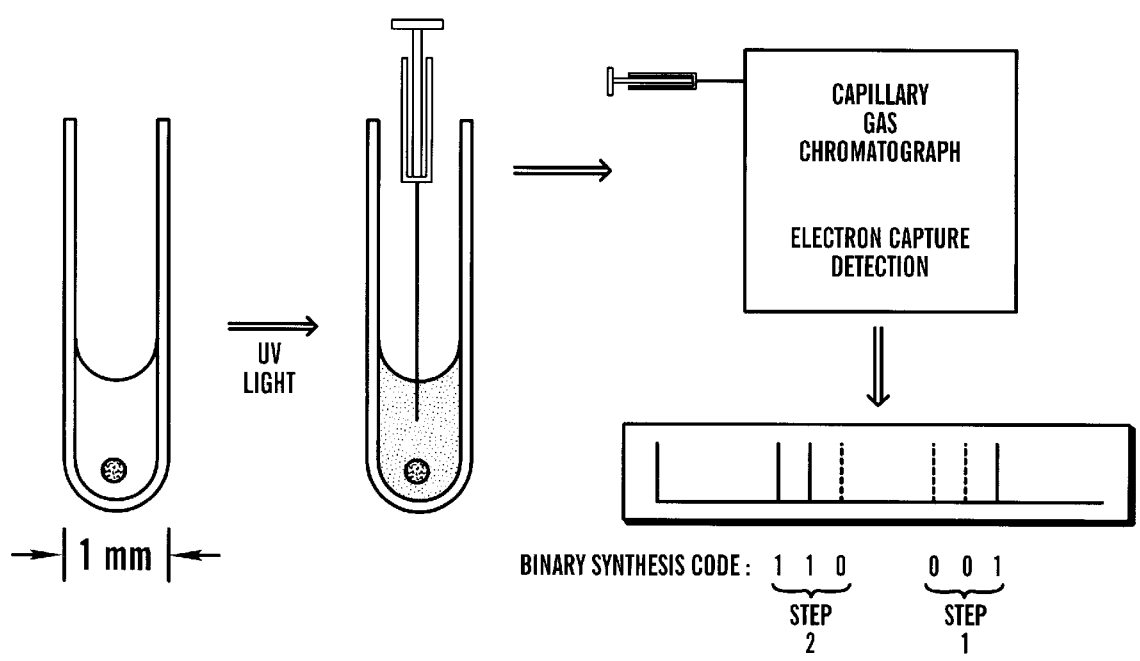
FIG. 5.
Figure 6:
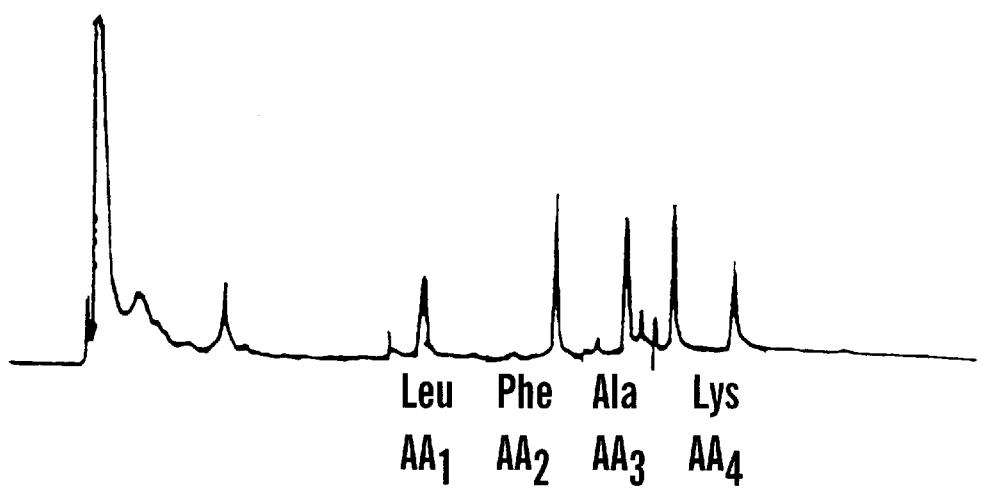
FIG. 6.

After receptor beads are treated with a substrate which has a color dye attached on it, the bead binding the substrate is stained and can be easily identified in a background of many colorless beads. The stained bead is then removed from the library by a microsyringe, and subjected to decode to identify its structure. The decoding process involves three operations: a) photolysis of the beads, b) silylation of liberated alcohols, c) injection into GC-EC machine. Once identified, the receptor is then resynthesized on large quantities of beads for confirmatory binding studies. FIG. 5 shows the process used to read the molecular bar code of a typical bead and in FIG. 6 the typical gas chromatography for a bead is shown. From this spectrum, the structure of the receptor is identified as $C_3$-OGLY-leu-phe-Ac, $C_7$-OGLY-ala-Lys-Ac.

The Gly-receptor library was first treated with dye-derivated serine 17 shown below, it was found that more than 50% beads stained as orange color. It is believed this nonspecific binding could be reduced either by screening the library with more functionalized and more conformationally defined substrates such as biointeresting peptides or by synthesizing another library whose binding conformation is more rigid.

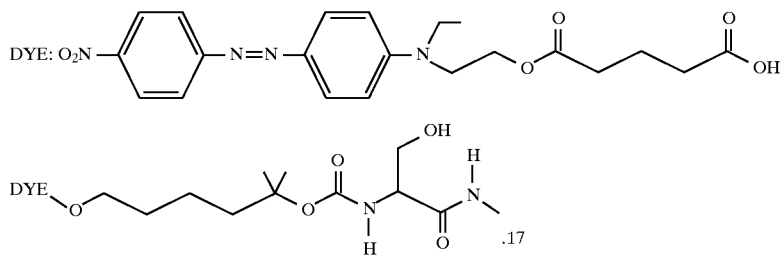

A Color Substrate for Screening the Libraries

The second receptor library (Pro-library) is shown in shown below.

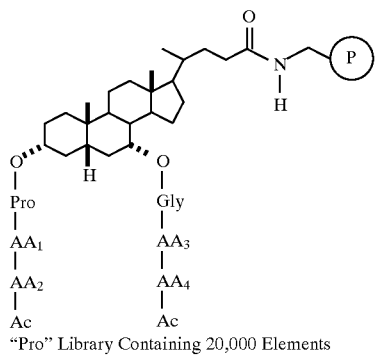

"Pro" Library Containing 20,000 Elements

It was expected that D or L proline at the first position of $C_3$-chain instead of glycine in the previous library would rigidity the $C_3$ chain. Therefore, the binding conformation for second receptor might be more defined than that of the first one.

The Gly-library was found to bind Leucine Enkephalin 18 and Met Enkephalin 19 very selectively.

pentapeptides. In contrast to the above case of "serine" binding, the percentage of stained beads is 0.65% for Leucine Enkephalin and 0.53% for Met Enkephalin. 17 active beads against Leu Enkephalin and 28 active beads against Met Enkephalin were retrieved from the Gly library and decoded. The sequences of two peptide chains are summarized in Table 1 and 2.

TABLE 1

Protected Gly-library Binding with Leucine Enkephalin

| C3 Chain | C7 Chain | |
|---|---|---|
| GLY—ASP—PRO | GLY—PRO—GLU | (FOUND 5x) |
| GLY—ASP—PRO | GLY—PRO—VAL | (FOUND 3x) |
| GLY—PHE—PRO | GLY—PRO—LEU | (FOUND 3x) |
| GLY—LEU—PRO | GLY—PRO—LYS | (FOUND 2x) |
| GLY—PHE—PRO | GLY—PRO—PHE | |
| GLY—LEU—ALA | GLY—PRO—VAL | |
| GLY—LEU—PRO | GLY—PRO—ALA | |
| GLY—PHE—LYS | GLY—PRO—GLU | |
| GLY—PHE—LYS | GLY—LYS—LEU | |
| GLY—PHE—PRO | GLY—PRO—GLU (BRIGHT) | (FOUND 2x) |
| GLY—ASP—VAL | GLY—PRO—GLU | |
| GLY—PHE—SER | GLY—PRO—PHE | |
| GLY—ASP—VAL | GLY—PRO—LEU | |
| GLY—VAL—VAL | GLY—PRO—VAL | |

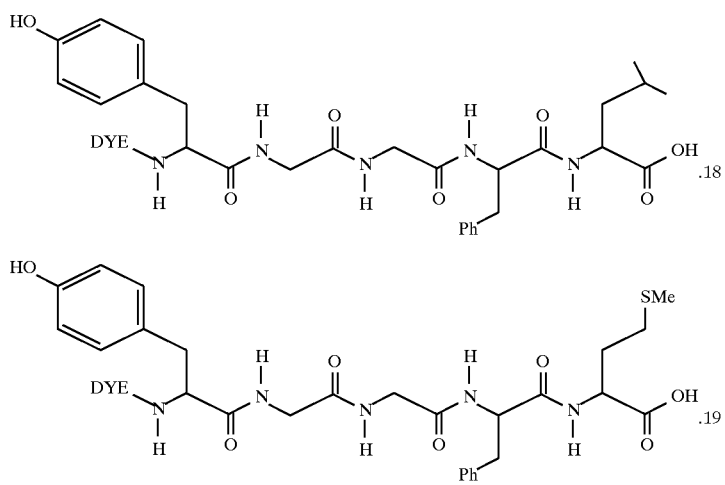

Enkephalin is an important neuropeptide (Leu Enkephalin and Met Enkephalin are both commercially available from Bachem, Inc; Fodor, S. P. A.; Read, J. L.; Pirrung, M. C.; Stryer, L.; Lu, A. T. and Solas, D. *Science* 1991, 251, 767; Hughes, J.; Smith, T. W.; Kosterlitz, H. W.; Fothergill, L. A.; Morgan, B. A. and Morrio, H. R. *Nature*, 1975, 258, 577). It is a natural ligand for an opiate receptor composed of two

TABLE 1-continued

Protected Gly-library Binding with Leucine Enkephalin

| | |
|---|---|
| GLY—LEU—PRO | GLY—PRO—LEU |
| GLY—VAL—VAL | GLY—PRO—LYS |
| GLY—GLU—PRO | GLY—PRO—LEU |
| GLY—ASP—VAL | GLY—PRO—ALA |
| GLY—ASP—PRO | GLY—PRO—PHE |
| GLY—PRO—PRO | GLY—PRO—PHE |
| GLY—PRO—LYS | GLY—PRO—VAL |
| GLY—VAL—SER | GLY—SER—GLU |
| GLY—PHE—SER | GLY—PRO—PHE |
| GLY—PRO—PRO | GLY—THR—PRO |
| GLY—LEU—VAL | GLY—LEU—PRO |
| GLY—SER—ALA | GLY—PRO—ALA |
| GLY—ALA—PRO | GLY—PRO—PHE |
| GLY—ASP—PRO | GLY—PRO—LEU |
| GLY—ASP—VAL | GLY—PRO—THR |
| GLY—LEU—PRO | GLY—PRO—VAL |
| GLY—LEU—PHE | GLY—ALA—LYS |
| GLY—LYS—VAL | GLY—LYS—THR |
| GLY—PHE—PRO | GLY—PRO—PRO |

STATISTICS

| | | | | |
|---|---|---|---|---|
| ALA | 2% | 5% | 2% | 7% |
| VAL | 7% | 18% | 0% | 21% |
| LEU | 23% | 0% | 2% | 21% |
| PHE | 27% | 2% | 0% | 16% |
| PRO | 7% | 61% | 86% | 7% |
| SER | 2% | 7% | 2% | 0% |
| THR | 0% | 0% | 2% | 5% |
| LYS | 5% | 7% | 5% | 12% |
| GLU | 2% | 0% | 0% | 14% |
| ASP | 27% | 0% | 0% | 0% |

TABLE 2

Protected Gly-library Binding with Met Enkephalin

| C3 CHAIN | C7 CHAIN | |
|---|---|---|
| GLY—LYS—PRO | GLY—PRO—VAL | |
| GLY—PHE—PRO | GLY—PRO—GLU | (FOUND 2x) |
| GLY—THR—PRO | GLY—ALA—PHE | |
| GLY—PRO—LEU | GLY—PRO—LEU | |
| GLY—ASP—VAL | GLY—PRO—LYS | |
| GLY—PHE—ALA | GLY—PRO—LYS | (FOUND 2x) |
| GLY—PHE—PRO | GLY—PRO—ALA | |
| GLY—PHE—PRO | GLY—PRO—LEU | (FOUND 2x) |
| GLY—LEU—PRO | GLY—PRO—LEU | (FOUND 2x) |
| GLY—PHE—PRO | GLY—PRO—LYS | |
| GLY—PHE—PRO | GLY—PRO—PHE | |
| GLY—LYS—SER | GLY—PRO—LEU | |
| GLY—PRO—GLU | GLY—PRO—PHE | |
| GLY—ASP—PRO | GLY—PRO—VAL | (FOUND 2x) |
| GLY—ASP—PRO | GLY—PRO—LEU | |
| GLY—ASP—PRO | GLY—PRO—PHE | |
| GLY—ASP—PRO | GLY—PRO—GLU | |
| GLY—LYS—SER | GLY—PRO—LYS | |
| GLY—PHE—SER | GLY—PRO—VAL | |
| GLY—THR—PRO | GLY—PRO—LEU | |
| GLY—LEU—ALA | GLY—PRO—PRO | |
| GLY—VAL—PRO | GLY—PRO—PRO | |
| GLY—PRO—PRO | GLY—PRO—PRO | |
| GLY—ALA—LYS | GLY—PRO—VAL | |
| GLY—PHE—PRO | GLY—PRO—VAL | |
| GLY—GLU—PRO | GLY—PRO—VAL | |
| GLY—ASP—VAL | GLY—PRO—VAL | (FOUND 2x) |
| GLY—ASP—LEU | GLY—PRO—VAL | (FOUND 2x) |
| GLY—VAL—LYS | GLY—PRO—LYS | |
| GLY—GLU—ALA | GLY—PRO—VAL | |
| GLY—ASP—ALA | GLY—PRO—ALA | |
| GLY—ASP—LEU | GLY—LEU—SER | |
| GLY—LEU—LYS | GLY—ALA—PRO | |
| GLY—ASP—LYS | GLY—ALA—PRO | |
| GLY—PRO—PRO | GLY—ALA—ASP | |

TABLE 2-continued

Protected Gly-library Binding with Met Enkephalin

| | |
|---|---|
| GLY—VAL—PRO | GLY—ALA—LEU |
| GLY—ALA—PRO | GLY—VAL—PRO |
| GLY—PHE—PRO | GLY—VAL—PRO |
| GLY—ALA—VAL | GLY—VAL—PRO |
| GLY—ALA—PRO | GLY—GLU—ALA |
| GLY—THR—PRO | GLY—LYS—VAL |
| GLY—VAL—LYS | GLY—PHE—ALA |

Statistics

| | | | | |
|---|---|---|---|---|
| ALA | 8% | 10% | 10% | 8% |
| VAL | 8% | 8% | 6% | 27% |
| LEU | 8% | 8% | 2% | 18% |
| PHE | 24% | 0% | 2% | 8% |
| PRO | 8% | 55% | 86% | 16% |
| SER | 0% | 6% | 0% | 2% |
| THR | 6% | 0% | 0% | 0% |
| LYS | 6% | 10% | 2% | 12% |
| GLU | 4% | 2% | 2% | 6% |
| ASP | 27% | 0% | 0% | 2% |

From Table 1 and 2, proline is the most common amino acid residue in both Leu and Met Enkephalin receptors. Proline, especially at the second position of $C_7$ chain, plays an important role in defining the binding conformation of receptors. However, the second most common amino acid residues are different in Leu and Met Enkephalin receptors. For Leu Enkephalin receptors, they are leucine on the $C_3$ chain and lysine on the $C_7$ chain, but they are aspartic acid on the $C_3$ chain and valine on the $C_7$, chain in Met Enkephalin receptors. Another striking finding is that one of the receptors against Leu Enkephalin overlap with those found to recognize Met Enkephalin. This observation implies that the receptors selected by screening may have selectivity to their own ligand.

When treated with Leu Enkephalin 18, the bead containing either protected to deprotected $C_3$-OGLY-Lys-Pro-Lys-Ac, receptor was stained intensively. Thus this receptor was resynthesized on 200 mg of beads to confirm the binding results. After treating 5 mg of the resulting beads with 500 $\mu$L, 620 $\mu$M solution of Leu Enkephalin 18 at room temperature for 1 hour, the beads collected all the color substrates from the solution and the solution became colorless. Another 5 mg of the above beads was treated with 500 $\mu$L, 620 $\mu$M solution of Met Enkephalin, after 2 hours at room temperature, the beads became red color and the solution was slightly orange. Although no quantitative measurement of the selective binding of $C_3$-OGLY-Lys-Pro-Ac, $C_7$-OGLY-Pro-Lys-Ac receptor to Leu and Met Enkephalin were performed. It appears that the receptor bound Leu Enkephalin will be further increased by making a more diverse library. This can be easily achieved by using more chemical steps to extend the peptide chains and more monomers in each step.

The Pro-library was screened by Leu Enkephalin 18 and Met Enkephalin 19. There were about 0.75% beads stained by Leu Enkephalin and 0.4% by Met Enkephalin.

The results are listed in Table 3 and 4. The sequences of receptors are listed in the experimental section.

TABLE 3

Protected Pro-library Binding With Leu Enkephalin (32 retrieved beads).

L-Proline, 15 beads

| $C_3$ Chain | $C_7$ Chain | |
|---|---|---|
| L-PRO—VAL—VAL | GLY—ALA—ALA | |
| L-PRO—VAL—LYS | GLY—ALA—ALA | |
| L-PRO—PHE—LYS | GLY—ALA—ALA | |
| L-PRO—GLU—LYS | GLY—SER—ALA | |
| L-PRO—ALA—PHE | GLY—SER—ALA | |
| L-PRO—THR—ALA | GLY—SER—ALA | |
| L-PRO—THR—ALA | GLY—PHE—ALA | (×2) |
| L-PRO—THR—PHE | GLY—PHE—ALA | |
| L-PRO—PHE—PHE | GLY—PHE—ALA | |
| L-PRO—SER—ALA | GLY—LYS—ALA | |
| L-PRO—VAL—ALA | GLY—LYS—ALA | |
| L-PRO—SER—LYS | GLY—VAL—VAL | |
| L-PRO—VAL—PHE | GLY—VAL—LYS | |
| L-PRO—VAL—VAL | GLY—LYS—LYS | |

Statistics

| | | | | |
|---|---|---|---|---|
| ALANINE | 7% | 33% | 20% | 87% |
| VALINE | 20% | 13% | 13% | 0% |
| LEUCINE | 0% | 0% | 0% | 0% |
| PHENYLALANINE | 13% | 27% | 27% | 0% |
| PROLINE | 0% | 0% | 0% | 0% |
| SERINE | 13% | 0% | 20% | 0% |
| THREONINE | 27% | 0% | 0% | 0% |
| LYSINE | 0% | 27% | 13% | 13% |
| GLUTAMIC ACID | 7% | 0% | 0% | 0% |
| ASPARTIC ACID | 0% | 0% | 0% | 0% |

D-Proline, 17 beads

| C3 Chain | C7 Chain | |
|---|---|---|
| D-PRO—SER—LYS | GLY—ALA—ALA | (×2) |
| D-PRO—ALA—ALA | GLY—ALA—ALA | |
| D-PRO—SER—PHE | GLY—GLU—ALA | |
| D-PRO—SER—ALA | GLY—GLU—ALA | |
| D-PRO—SER—GLU | GLY—SER—ALA | |
| D-PRO—SER—ALA | GLY—SER—ALA | |
| D-PRO—PHE—PHE | GLY—SER—ALA | |
| D-PRO—PHE—LYS | GLY—PHE—ALA | (×2) |
| D-PRO—SER—LYS | GLY—PHE—ALA | |
| D-PRO—SER—GLU | GLY—PHE—ALA | |
| D-PRO—VAL—VAL | GLY—LYS—ALA | |
| D-PRO—THR—LYS | GLY—GLU—ALA | |
| D-PRO—ALA—LYS | GLY—GLU—GLU | |
| D-PRO—VAL—ALA | GLY—PHE—GLU | |

Statistics

| | $C_3$ Chain | | $C_7$ Chain | |
|---|---|---|---|---|
| Ala | 12% | 35% | 18% | 88% |
| Val | 12% | 0% | 0% | 0% |
| Leu | 0% | 0% | 0% | 0% |
| Phe | 24% | 12% | 35% | 0% |
| Pro | 0% | 0% | 0% | 0% |
| Ser | 47% | 0% | 18% | 0% |
| Thr | 6% | 0% | 0% | 0% |
| Lys | 0% | 41% | 6% | 0% |
| Glu | 0% | 12% | 24% | 12% |
| Asp | 0% | 0% | 0% | 0% |

TABLE 4

The selected receptors from Pro-library for Met Enkephalin are shown below:

L-Proline (6 beads)

| C3 Chain | C7 Chain |
|---|---|
| L-PRO—ASP—PRO | GLY—PRO—PRO |
| L-PRO—VAL—PHE | GLY—ALA—ALA |
| L-PRO—GLU—THR | GLY—ALA—ALA |
| L-PRO—LEU—PRO | GLY—LEU—ALA |
| L-PRO—ALA—PRO | GLY—PRO—ALA |
| L-PRO—GLU—ALA | GLY—LYS—PRO |

Statistics

| | $C_3$ Chain | | $C_7$ Chain | |
|---|---|---|---|---|
| Ala | 16% | 16% | 32% | 66% |
| Val | 16% | 0% | 0% | 0% |
| Leu | 16% | 0% | 16% | 0% |
| Phe | 0% | 16% | 0% | 0% |
| Pro | 0% | 48% | 32% | 33% |
| Ser | 0% | 16% | 0% | 0% |
| Thr | 0% | 0% | 0% | 0% |
| Lys | 0% | 0% | 16% | 0% |
| Glu | 32% | 0% | 0% | 0% |
| Asp | 16% | 0% | 0% | 0% |

D-Proline (10 beads)

| C3 Chain | C7 Chain |
|---|---|
| D-PRO—ALA—ALA | GLY—PHE—ALA |
| D-PRO—THR—LYS | GLY—PHE—ALA |
| D-PRO—LEU—PRO | GLY—PRO—PRO |
| D-PRO—ALA—PRO | GLY—ALA—ALA |
| D-PRO—PRO—PRO | GLY—PHE—ALA |
| D-PRO—SER—ALA | GLY—ALA—ALA |
| D-PRO—PRO—PRO | GLY—LYS—GLU |
| D-PRO—ALA—ALA | GLY—ALA—ALA |
| D-PRO—THR—ALA | GLY—ALA—PRO |

Statistics

| | $C_3$ Chain | | $C_7$ Chain | |
|---|---|---|---|---|
| Alanine | 40% | 50% | 50% | 60% |
| Valine | 0% | 0% | 0% | 0% |
| Leucine | 10% | 0% | 30% | 0% |
| Phenylalanine | 0% | 0% | 0% | 0% |
| Proline | 20% | 40% | 10% | 30% |
| Serine | 10% | 0% | 0% | 0% |
| Threonine | 20% | 0% | 0% | 0% |
| Lysine | 0% | 10% | 10% | 0% |
| Glutamic acid | 0% | 0% | 0% | 10% |
| Aspartic acid | 0% | 0% | 0% | 0% |

In contrast to the Gly-library, the most common residue in Proline-library is alanine at the third position on $C_7$ chain. Proline becomes one of the least common residues in Leu Enkephalin receptors. Again Leu and Met Enkephalin receptors do not have a common sequence.

The actual binding mode for our receptors binding Enkephalin is still unknown and very difficult to ascertain. However, our "artificial antibody" has been shown to be very promising in recognition of Leu and Met Enkephalin. It may provide an efficient chemical method to distinguish very subtle differences between molecules.

The subtle difference between Leu and Met make them very difficult to be recognized even by a natural receptor, and is almost impossible for rational design to develop receptors for then. Therefore, the methods described above may allow the development of receptors for almost any substrates even without knowing the exact shape, size and arrangement of functionalities involved.

Some additional binding studies for Peptidosteroidal receptors with beta-Casomorphinamide and Des-Tyr Leu Enkahphalin, are shown in the following table 5 and are compared to the Leu Enkaphalin and Met Enkaphalin.

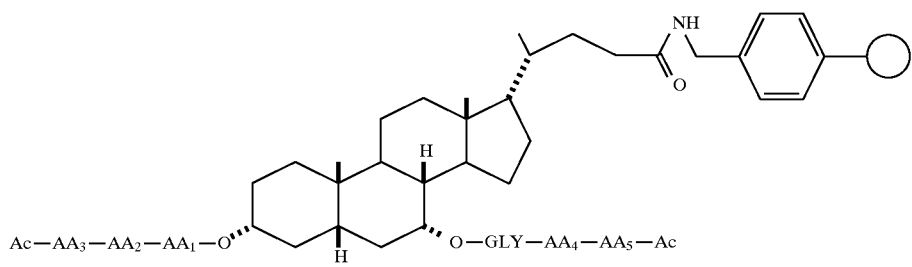

TABLE 5

PEPTIDOSTEROIDAL RECEPTORS WHICH SELECTIVELY BIND OPIOID PEPTIDES

| SUBSTRATE | BOUND | AA1 | AA2 | AA3 | AA4 | AA5 | $K_{D-MAX}$ |
|---|---|---|---|---|---|---|---|
| β-Casomorphinamide (Dye-TYR—PRO—PHE—NH$_2$) | 0.3% | GLY | PHE | PHE | ALA | ALA | 407 µM |
| Dee-TyR Leu Enkephalin (Dye-GLY—GLY—PHE—LEU) | 0.1% | GLY | LYS | ALA | ALA | LYS | 141 µM |
| Leu Enkephalin (Dye-TYR—GLY—GLY—PHE—LEU) | 0.7% | GLY | ASP | PRO | PRO | LEU | 81 µM |
| Met Enkephalin (Dye-TYR—GLY—GLY—PHE—MET) | 0.5% | GLY | PHE | PRO 95% | PRO | LEU | 85 µM |
| | 0.8% | PRO | THR | LYS | PHE | ALA 90% | 75 µM |

EXAMPLE 2

Preparation of a Macrocyclic Synthetic Receptor

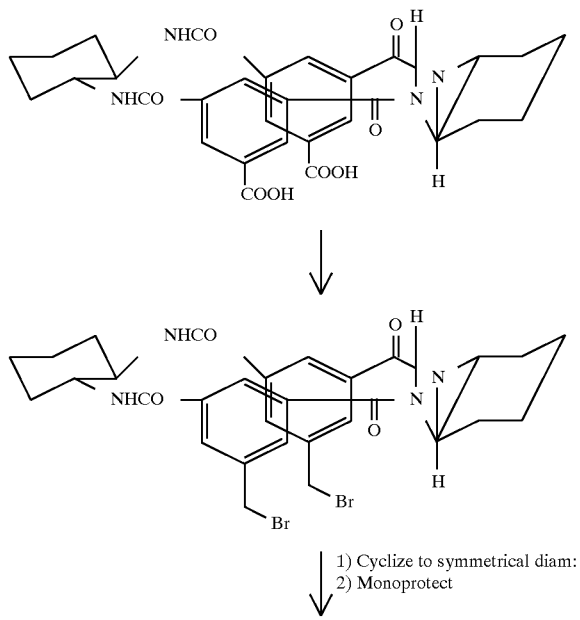

1) Cyclize to symmetrical diam:
2) Monoprotect

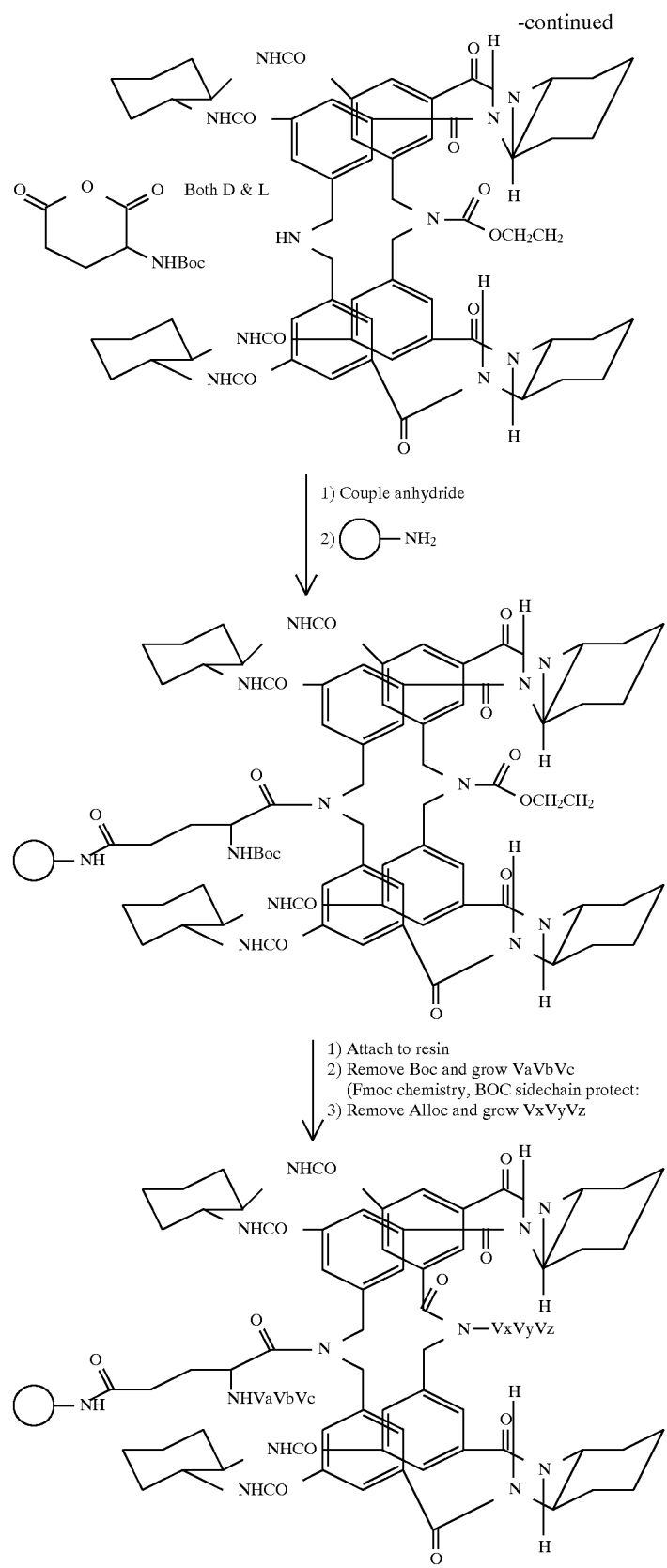

EXAMPLE 3

Preparation of a polyfunctional organic template that is water-soluble. The alpha hydroxyls at positions 3 and 12 are attached to the oligomer chains and the carboxyl group may be use in linking the synthetic receptor to a solid support.

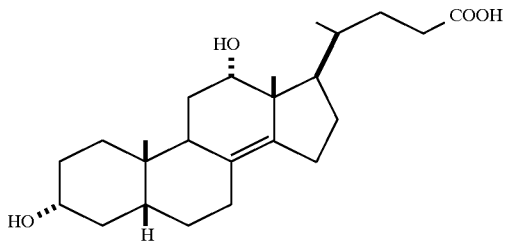

↓

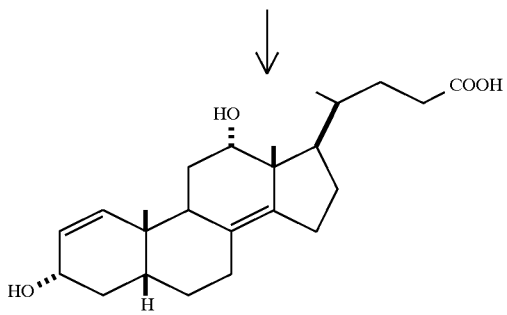

↓

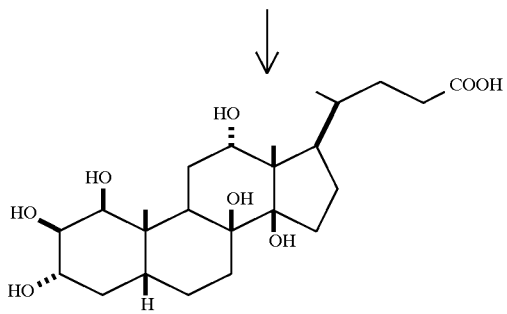

What is claimed is:

1. A synthetic receptor which comprises a polyfunctional organic template covalently linked to two or more oligomer which may independently be straight chained or branched oligoamide, oligoester, oligourea, oligourethane, oligoamine, oligoether, oligosulfonamide, oligophosphonamide, oligophoephonate, oligophqsphate, oligonucleotide, oligosaccharide, peptide oligomer, or a mixture of monomers thereof; wherein each oligomer independently contains 2 to 10 monomers; and wherein the polyfunctional organic template is a polycarbocyclic.

2. The synthetic receptor of claim 1, wherein at least one of the oligomers is a combination of two or more distinct classes of oligomers selected from the group consisting of an oligoamide, an oligoester, an oligourea, an oligourethane, an oligoamine, an oligoether, an oligosulfonamide, an oligophosphonamide, an oligophosphonate, an oligophosphate, an oligonucleotide, an oligosaccharide and a peptide oligomer.

3. The synthetic receptor of claim 1, wherein the oligomers are different.

4. The synthetic receptor of claim 1, wherein the oligomers are the same.

5. A synthetic receptor which comprises a polyfunctional steroid template covalently linked to two or more peptide oligomers which may independently be the same or different and which may independently be straight chain or branched.

6. The synthetic receptor of claim 5, wherein the polyfunctional steroid template is ursodeoxycholic acid, hyodeoxycholic acid, alpha-apocholic acid,

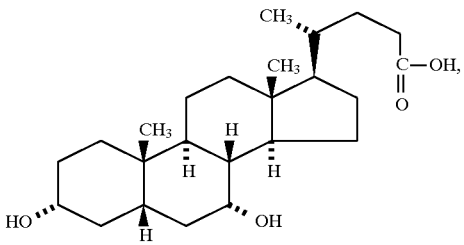

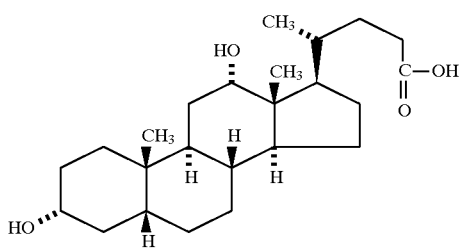

or

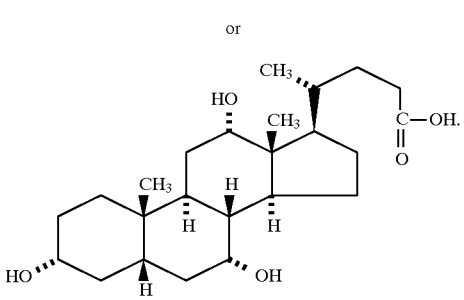

7. The synthetic receptor of claim 5, wherein at least two of said two or more peptide okugomers comprise at least two amino acids.

8. The synthetic receptor of claim 1, wherein the polyfunctional organic template is further linked to a dye, a fluorescent label or a radioactive label.

9. The synthetic receptor of claim 1, wherein the polyfunctional organic template is further linked to an identifier which uniquely defines the synthetic receptor.

10. The synthetic receptor of claim 9, wherein the identifier uniquely defines the synthesis and molecular structure of the oligomers of the synthetic receptor.

11. The synthetic receptor of claim 9, wherein the identifier is a stable chemical molecule or a plurality of stable chemical molecules distinguishable and detectable to picomolar levels.

12. The synthetic receptor of claim 9, wherein the identifier is an oligonucleotide.

13. The synthetic receptor of claim 5, wherein the polyfunctional steroid template is covalently linked to a solid support.

14. The synthetic receptor of claim 13, wherein the solid support is polystyrene or PEG-polystyrene particles.

* * * * *